United States Patent
Saroka et al.

(10) Patent No.: US 10,307,102 B2
(45) Date of Patent: Jun. 4, 2019

(54) THORACIC GARMENT OF POSITIONING ELECTROMAGNETIC (EM) TRANSDUCERS AND METHODS OF USING SUCH THORACIC GARMENT

(71) Applicant: Sensible Medical Innovations Ltd., Kfar Neter (IL)

(72) Inventors: Amir Saroka, Tel-Aviv (IL); Leonid Voshin, Kfar-Saba (IL); Jonathan Bar-Or, Pardes Hana (IL); Tal Levi, Tel-Aviv (IL); Ofer Karp, Haifa (IL); Yiftach Barash, Tel-Aviv (IL); Nadav Mizrahi, Tel-Aviv (IL); Dan Rappaport, Tel-Aviv (IL); Shlomi Bergida, Udim (IL); Jonathan Bahat, Omer (IL)

(73) Assignee: Sensible Medical Innovations Ltd., Netanya (IL)

( * ) Notice: Subject to any disclaimer, the term of this patent is extended or adjusted under 35 U.S.C. 154(b) by 0 days.

(21) Appl. No.: 14/366,704

(22) PCT Filed: Dec. 20, 2012

(86) PCT No.: PCT/IL2012/050545
§ 371 (c)(1),
(2) Date: Jun. 19, 2014

(87) PCT Pub. No.: WO2013/093923
PCT Pub. Date: Jun. 27, 2013

(65) Prior Publication Data
US 2014/0378812 A1    Dec. 25, 2014

Related U.S. Application Data

(60) Provisional application No. 61/604,627, filed on Feb. 29, 2012, provisional application No. 61/577,782, filed on Dec. 20, 2011.

(51) Int. Cl.
*A61B 5/00* (2006.01)
*A61B 5/05* (2006.01)
*A61B 5/053* (2006.01)

(52) U.S. Cl.
CPC .......... *A61B 5/6805* (2013.01); *A61B 5/053* (2013.01); *A61B 5/0507* (2013.01);
(Continued)

(58) Field of Classification Search
CPC .......... A61N 1/00; A61K 9/00; A61B 5/0402; A61B 5/0225; A61B 5/022; A61B 5/05
See application file for complete search history.

(56) References Cited

U.S. PATENT DOCUMENTS

| | | | | |
|---|---|---|---|---|
| 4,188,944 A | * | 2/1980 | Augustyniak | A61F 5/3738 602/20 |
| 4,381,012 A | * | 4/1983 | Russek | A61N 1/22 600/382 |

(Continued)

FOREIGN PATENT DOCUMENTS

| | | |
|---|---|---|
| CN | 1852677 | 10/2006 |
| CN | 1886090 | 12/2006 |

(Continued)

OTHER PUBLICATIONS

Halperin et al. Preliminary study of cardiopulmonary resuscitation by circumferential compression of the chest with the use of a pneumatic vest. 1993 New Eng.J.Med. 329:762-768.*

(Continued)

*Primary Examiner* — Tse W Chen
*Assistant Examiner* — Patrick M Mehl

(57) ABSTRACT

A garment for bringing an EM transducer to contact with a thoracic skin surface area of a wearer is disclosed. The garment comprises a thoracic garment having a EM transducer placement portion and a pressure applying element (Continued)

associated with the EM transducer placement portion for applying a pressure on an EM transducer secured in an associated the EM transducer placement portion when the thoracic garment is worn by a wearer so that the EM transducer applies a respective pressure on a thoracic skin surface area of the wearer.

23 Claims, 12 Drawing Sheets

(52) U.S. Cl.
CPC .......... *A61B 5/6823* (2013.01); *A61B 5/6843* (2013.01); *A61B 5/6844* (2013.01)

(56) References Cited

U.S. PATENT DOCUMENTS

| | | | | |
|---|---|---|---|---|
| 5,968,527 | A * | 10/1999 | Litovitz | A61K 38/1709 424/1.11 |
| 6,701,185 | B2 * | 3/2004 | Burnett | A61N 1/36071 607/149 |
| 6,757,916 | B2 | 7/2004 | Mah et al. | |
| 2004/0077937 | A1 * | 4/2004 | Yarden | A61B 5/04 600/386 |
| 2004/0210165 | A1 | 10/2004 | Marmaropoulos et al. | |
| 2005/0059896 | A1 * | 3/2005 | Drakulic | A41D 13/1281 600/509 |
| 2005/0154336 | A1 | 7/2005 | Kloecker et al. | |
| 2005/0275416 | A1 * | 12/2005 | Hervieux | A41D 13/1281 324/663 |
| 2008/0194917 | A1 | 8/2008 | Muehlsteff et al. | |
| 2008/0287770 | A1 | 11/2008 | Kurzweil et al. | |
| 2010/0042026 | A1 * | 2/2010 | Kloecker | A61F 5/34 601/149 |
| 2010/0324429 | A1 * | 12/2010 | Leschinsky | A61B 5/02208 600/493 |
| 2011/0130800 | A1 | 6/2011 | Weinstein et al. | |

FOREIGN PATENT DOCUMENTS

| | | |
|---|---|---|
| CN | 101163442 | 4/2008 |
| WO | WO 2006/111875 | 10/2006 |
| WO | WO 2009/031149 | 3/2009 |
| WO | WO 2013/093923 | 6/2013 |

OTHER PUBLICATIONS

Halperin et al. 1993 New Eng..J..Med.. 329:762-768.*
Communication Relating to the Results of the Partial International Search dated Mar. 28, 2013 From the International Searching Authority Re. Application No. PCT/IL2012/050545.
International Search Report and the Written Opinion dated Jun. 17, 2013 From the International Searching Authority Re. Application No. PCT/IL2012/050545.
International Preliminary Report on Patentability dated Jul. 3, 2014 From the International Bureau of WIPO Re. Application No. PCT/IL2012/050545.
Notification of Office Action and Search Report dated Dec. 31, 2015 From the State Intellectual Property Office of the People's Republic of China Re. Application No. 201280070264.3 and Its Summary of Office Action in English.
Communication Pursuant to Article 94(3) EPC dated Nov. 30, 2015 From the European Patent Office Re. Application No. 12821060.6.
Communication Pursuant to Article 94(3) EPC dated Oct. 18, 2016 From the European Patent Office Re. Application No. 12821060.6.
Notification of Office Action and Search Report dated Oct. 31, 2016 From the State Intellectual Property Office of the People's Republic of China Re. Application No. 201280070264.3 and Its Summary of Office Action in English. (15 Pages).
Communication Pursuant to Article 94(3) EPC dated Jun. 21, 2017 From the European Patent Office Re. Application No. 128210606. (4 Pages)
Office Action dated Feb. 13, 2018 From the Israel Patent Office Re. Application No. 233301 and Its Translation Into English. (8 Pages).

* cited by examiner

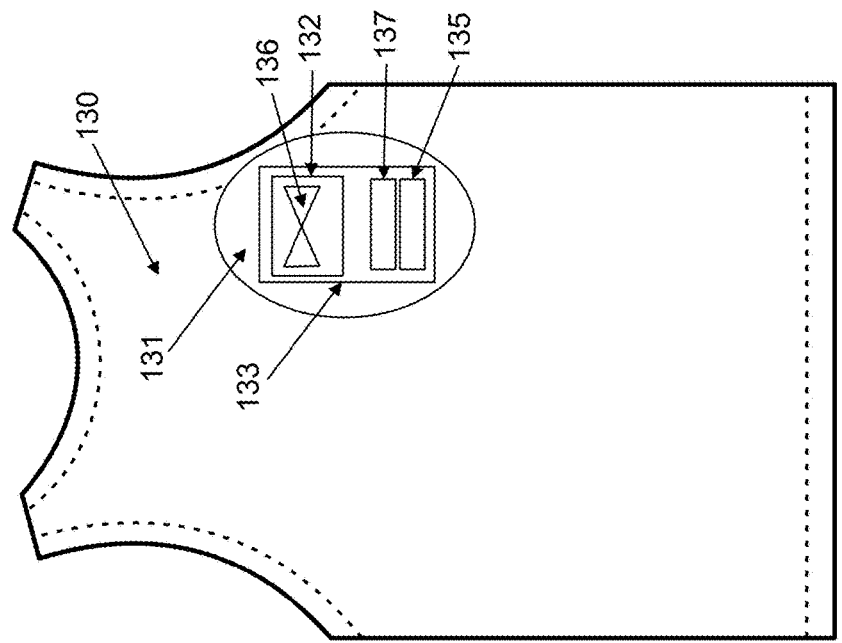
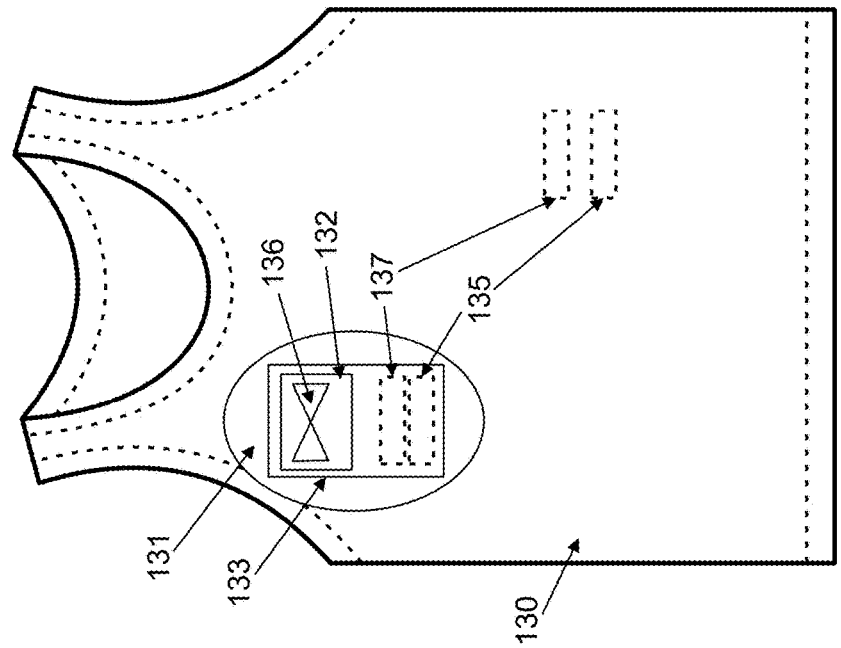

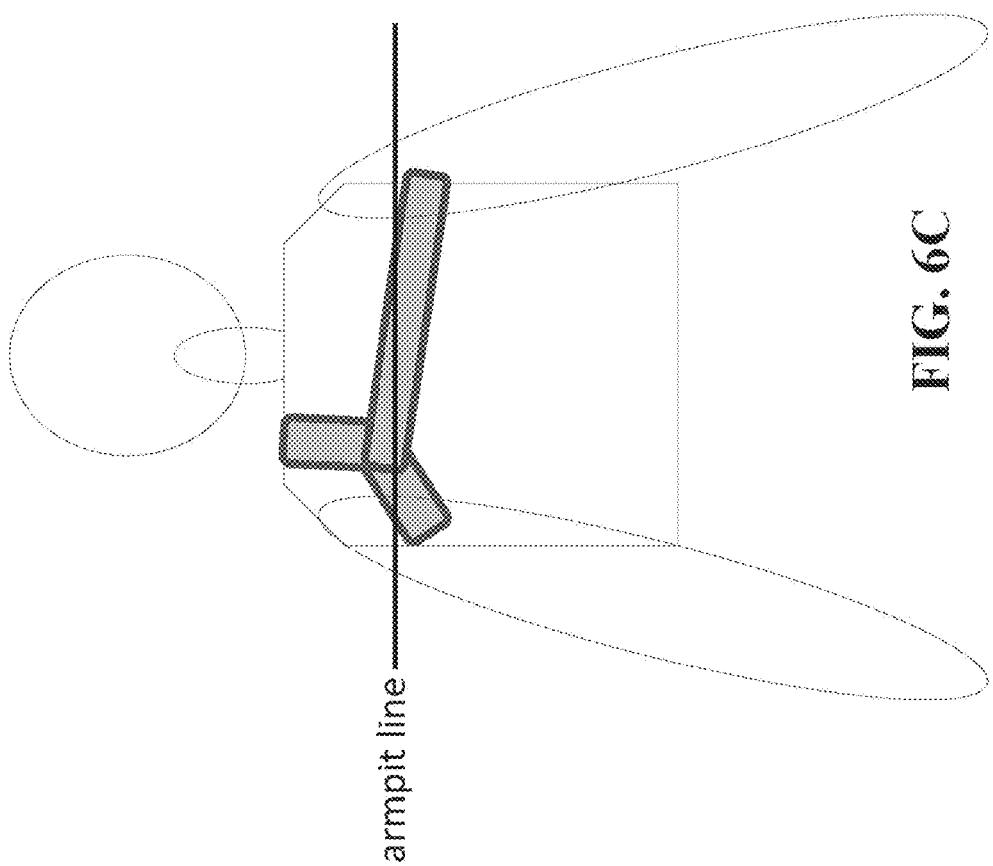

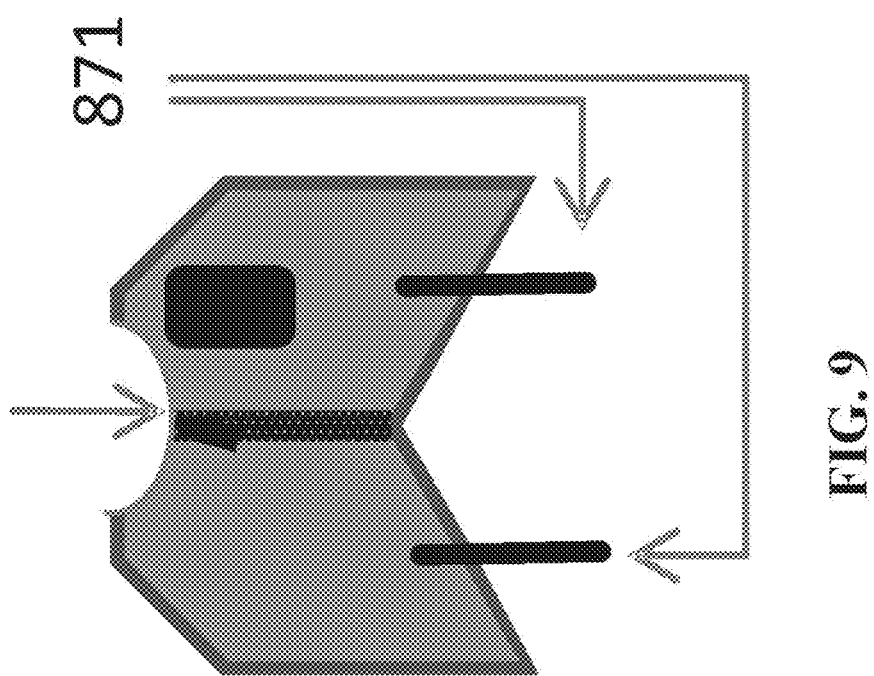

THORACIC GARMENT OF POSITIONING ELECTROMAGNETIC (EM) TRANSDUCERS AND METHODS OF USING SUCH THORACIC GARMENT

RELATED APPLICATION APPLICATIONS

This application is a National Phase of PCT Patent Application No. PCT/IL2012/050545 having international filing date of Dec. 20, 2012 which claims the benefit of priority under 35 USC § 119(e) of U.S. Provisional Patent Application No. 61/577,782 filed on Dec. 20, 2011 and 61/604,627 filed on Feb. 29, 2012. The content of the above applications are all incorporated by reference as if fully set forth herein.

FIELD AND BACKGROUND OF THE INVENTION

The present invention, in some embodiments thereof, relates to EM transducers positioning and, more particularly, but not exclusively, to a thoracic garment of positioning electromagnetic (EM) transducers and methods of using such a thoracic garment.

In various illnesses or situations, it is expedient to monitor a person or patient for diagnostic and therapeutic purposes. The monitoring may involve cardiac functions of respiration, skin resistance, transpiration, body temperature and the like. Depending on the type of illness or situation monitored, a mix of parameters is measured continuously over a period of more than a few minutes. This may require that sensors placed on the body would not significantly impair the comfort and the normal freedom of movement.

SUMMARY OF THE INVENTION

According to some embodiments of the present invention, there is provided a thoracic garment for bringing an EM transducer to contact with a thoracic skin surface area of a wearer. The thoracic garment comprises a thoracic garment having an EM transducer and a pressure applying element associated with the EM transducer for applying a pressure on the EM transducer when the thoracic garment is worn by a wearer so that the EM transducer applies a respective pressure on a thoracic skin surface area of the wearer.

Optionally, the pressure applying element comprises a strap configured to attach the thoracic garment to the wearer in one of a plurality of positions each applying a different of a plurality of pressures on the wearer.

Optionally, the thoracic garment comprises a controller configured to allow the pressure adjusting element to increase the pressure at least until an anterior surface of the EM transducer is in full surface contact with a skin surface of the wearer and to maintain the respective pressure at during a sensing period.

Optionally, the pressure applying element is associated with a controller set to control a degree of the pressure.

More optionally, thoracic garment comprises an undressing detector for detecting an undressing event, the controller reduces the pressure in response to the undressing event.

More optionally, the controller is set to allow transmitting of EM energy to or by the EM transducer when the pressure is within a predefined range.

Optionally, the thoracic garment is associated with a controller set to adjust the pressure to maintain the respective pressure above a predetermined threshold during a period of measurements held using the EM transducer.

Optionally, the respective pressure is above the predetermined threshold if it applies a force of between 0.2 Kg and 8 Kg to the skin of the wearer or between 0.3 and 5 Kg or between 0.4 Kg and 3 Kg.

Optionally, the skin surface of the wearer on which the pressure is applied is between 0.7 cm$^2$ and 200 cm$^2$. Optionally, the skin surface of the wearer on which the pressure is applied is essentially circular, having a diameter between 0.5 cm and 8 cm or between 2 and 8 cm or between 3 and 7 cm.

Optionally, the pressure applying element comprises an extendable member positioned between an anchoring element and the EM transducer, the extendable member having an adjustable length which changes a distance between an anchoring surface and the EM transducer.

More optionally, the adjustable length is between about 1 cm and about 10 cm or between about 2 centimeters (cm) and about 5 cm.

More optionally, the extendable member is an inflatable member and wherein the adjusting includes adjusting a fluid pressure within the inflatable member.

Optionally, the extendable member is an inflatable member constructed so as the contact surface between the inflatable member and the first object on which the inflatable member may exert pressure in the direction of a wearer's boy (e.g. a back surface of the EM transducer) does not reduce by more than 75% when the inflatable member is at the predetermined threshold as compared to the same inflatable member when deflated. Optionally the contact surface does not reduce by more than 50% or by more than 25%.

Optionally, the EM transducer structure comprises an EM transducer tilt matching mechanism.

Optionally, the pressure applying element comprises a plurality of EM transducers and a plurality of extendable members each positioned between an EM transducer and an anchoring surface such that a different pressure may be applied by one extendable member on a respective EM transducer than is applied on another extendable member on a respective EM transducer.

More optionally, the thoracic garment comprises a non-elastic thoracic portion having width of at least 3 centimeter and extends by no more than 60% of its length when attached to a load weighing 0.5 Kg.

Optionally, the thoracic garment has a plurality of EM transducer placement portions and a plurality of pressure applying elements associated with plurality of the EM transducer placement portions for applying a pressure on a plurality of EM transducers secured in the EM transducer placement portions when the thoracic garment being worn by the wearer so that each EM transducer applies the respective pressure on any of a plurality of thoracic skin surface areas of the wearer.

More optionally, a plurality of the plurality of EM transducers are comprised in a single array positioned in one of a posterior portion of the garment and an anterior portion of the garment.

More optionally, the plurality of EM transducers are comprised in a single array.

Optionally, the EM transducer placement portion is set to be placed above the skin surface of an anterior thoracic skin surface area such that at least 30% of an effective EM capture and/or transmission area of an EM transducer positioned in the EM transducer placement portion will be located between about 2 centimeters (cm) and about 9 cm to a side of a central axis along the sternum of the wearer and between about 2 cm and about 9 cm below the upper end of the manubrium of the wearer.

Optionally, the EM transducer placement portion is set to be placed above the skin surface of a posterior thoracic skin surface area such that at least 30% of an effective EM capture and/or transmission area of an EM transducer positioned in the EM transducer placement portion will be located between about 2 cm and about 9 cm to a side of a central axis along the spine of the wearer, and between about 8 cm and about 30 cm below the upper end of the vertebra prominens of the wearer.

According to some embodiments of the present invention, there is provided a set of thoracic garments, each defined as claimed in claim 1 and each being adjustable to fit different body shape and size.

According to some embodiments of the present invention, there is provided a thoracic garment for positioning at least one EM transducer on a body of a wearer. The thoracic garment comprises a thoracic garment portion sized and shaped to position at least one EM transducer at a predetermined location above a skin surface of a wearer and a controller which increases pressure of the at least one EM transducer on the skin surface after the thoracic garment is worn and reduces the pressure when the wearer undresses the thoracic garment. When the pressure is reduced a physically impaired wearer can self-dress the thoracic garment.

Optionally, when worn the wearer can recline and sit up freely while an effective EM capture and/or transmission area of the EM transducer is not displaced by more than 2 centimeters (cm).

Optionally, the thoracic garment further comprises at least one pulling strap extending from the thoracic garment.

Optionally, the thoracic garment comprises a belt for tightening the thoracic garment across the thorax of the wearer at a position below the sternum of the wearer when worn.

According to some embodiments of the present invention, there is provided a thoracic garment for positioning a plurality of EM transducers. The thoracic garment comprises a thoracic garment having a first EM transducer placement portion set to secure a first EM transducer and a second EM transducer placement portion set to secure a second EM transducer. When the thoracic garment is worn by a wearer and a first EM transducer is placed in the first EM transducer placement portion and a second EM transducer is placed in the second EM transducer placement portion: at least 30% of an effective EM capture and/or transmission area of the first EM transducer is located above skin surface of an anterior thoracic skin surface area located between about 2 centimeters (cm) and about 9 cm to a side of a central axis along the sternum of the wearer and between about 2 cm and about 9 cm below the upper end of the manubrium of the wearer and at least 30% of an effective EM capture and/or transmission area of the second EM transducer is located above skin surface of a posterior thoracic skin surface area located between about 2 cm and about 9 cm to a side of a central axis along the spine of the wearer, and between about 8 cm and about 30 cm below the upper end of the vertebra prominens of the wearer.

Optionally, the thoracic garment has at least one length adjusting element for fitting at least one portion of the thoracic garment to the body of the wearer and a fastener for allowing the wearer to wear and take off the thoracic garment without changing the fitting.

More optionally, the thoracic garment comprises an EM transducer secured in each of the first and second EM transducer placement portions.

Optionally, at least one of the first and second EM transducers is associated with an EM transducer moving mechanism for moving a respective of the first and second EM transducers or a portion thereof within the EM transducer placement portion.

Optionally, the EM transducers are positioned to measure a dielectric related property of lung tissue.

Optionally, the first EM transducer and the second EM transducer are on the same lateral side of the wearer's body.

Optionally, the garment is adjustable to fit a body shape and size of a wearer.

Optionally, when the thoracic garment is worn by a wearer to whom it was fitted, and at least one EM transducer is placed in the at least one EM transducer placement portion, the EM transducer is placed within ±2 cm from the predetermined location above the skin of the wearer for at least 50% of repeat wearing sessions without refitting.

Optionally, at least one of the first and second EM transducers is one of a plurality of EM transducers located in the first or second EM transducer placement portions and the thoracic garment comprises a controller for selecting one or more of the plurality of EM transducers according to the position of the EM transducers respective a body of a wearer.

According to some embodiments of the present invention, there is provided a thoracic garment for positioning an EM transducer. The thoracic garment comprises a thoracic garment having an EM transducer placement portion set to secure a first EM transducer. When the thoracic garment is worn by a wearer and the first EM transducer is placed in the EM transducer placement portion, at least 30% of an effective EM capture and/or transmission area of the EM transducer being above skin surface of a posterior thoracic skin surface area located between about 2 cm and about 9 cm to a side of a central axis along the spine of the wearer, and between about 8 cm and about 30 cm below the upper end of the vertebra prominens of the wearer.

Optionally, the thoracic garment further comprises an additional EM transducer placement portion set to secure an additional EM transducer wherein when the thoracic garment is worn by a wearer an additional EM transducer is placed in the additional EM transducer placement portion and at least 30% of an effective EM capture and/or transmission area of the additional EM transducer is located above skin surface of an anterior thoracic skin surface area located between about 2 centimeters (cm) and about 9 cm to a side of a central axis along the sternum of the wearer and between about 1 cm and about 9 cm below the upper end of the manubrium of the wearer.

According to some embodiments of the present invention, there is provided a method of monitoring a dielectric related property of a thoracic tissue. The method comprises dressing a wearer with a thoracic garment to secure a first EM transducer to a first location in proximity to an anterior thoracic skin surface area of the wearer and a second EM transducer to a posterior thoracic skin surface area of the wearer and analyzing an electromagnetic (EM) energy transmitted between the first and second EM transducers to identify a dielectric related property of at least one thoracic tissue. At least 30% of an effective EM capture and/or transmission area of the first EM transducer is located above the skin of the anterior thoracic body at an area between about 2 centimeters (cm) and about 9 cm to a side of a central axis along the sternum of the wearer, between about 2 cm and about 9 cm below the upper end of the manubrium of the wearer and the second EM transducer is placed located above the skin of the posterior thoracic skin surface area, between about 2 cm and about 9 cm to the side, between about 8 cm and about 30 cm below the upper end of the vertebra prominens of the wearer.

Optionally, the method further comprises fitting at least one portion of the thoracic garment to the body of the wearer to adjust the location of at least one of the first and second EM transducers in relation to the body of the wearer; and fixing the at least one fitted portion.

Optionally, the method further comprises redressing the wearer with the thoracic garment so that the first EM transducer and the second EM transducer are placed respectively above the skin surface of the anterior thoracic skin surface area and behind the posterior thoracic skin surface area without having to refit the at least one portion.

According to some embodiments of the present invention, there is provided a thoracic garment for positioning an EM transducer. The thoracic garment comprises a thoracic garment having an EM transducer placement portion, an EM transducer unit secured in the EM transducer placement portion and having an anchoring surface, an EM transducer placed adjacent the anchoring surface, and an extendable member between the anchoring surface and the EM transducer, the extendable member having an adjustable length which changes a distance between the anchoring surface and the EM transducer.

Optionally, the anchoring surface covers at least a part of the EM transducer.

Optionally, the anchoring surface further comprises a retracting element for retracting the EM transducer to reduce its distance from the anchoring surface.

Optionally, the EM transducer has a substantially rigid cup shaped structure placed so that an opening of the substantially rigid cup shaped structure faces the body of a wearer wearing the thoracic garment.

Optionally, the extendable member comprises at least one linear actuator.

More optionally, the extendable member has a pneumatic mechanism to adjust a pressure applied on the EM transducer.

More optionally, the EM transducer structure comprises an EM transducer tilt matching mechanism.

According to some embodiments of the present invention, there is provided a thoracic garment for positioning an EM transducer. The thoracic garment comprises a thoracic garment having anterior and posterior thoracic pieces, at least one EM transducer placement portion formed in at least one of the anterior thoracic piece and the posterior thoracic piece for securing an EM transducer, and a plurality of adjustable straps each connecting between a lateral side of the anterior thoracic piece and a lateral side of the posterior thoracic piece and having an adjustable length that sets the location of the at least one EM transducer placement portion in relation to at least one monitored intrabody region of a wearer wearing the thoracic garment.

Optionally, the anterior thoracic piece and the posterior thoracic piece are separable.

Optionally, at least one of the adjustable straps is an integral part of one of the anterior thoracic piece and the posterior thoracic piece, the at least one adjustable strap is configured to be detachably connected to at least one fastener connected to the other of the anterior thoracic piece and the posterior thoracic piece.

Optionally, the adjustable length is configured to be adjusted by positioning a first hook-and-loop fastener on one of the plurality of adjustable straps to a second hook-and-loop fastener.

More optionally, the thoracic garment further comprises a locking mechanism for locking at least one of the plurality of adjustable straps in a fixed state after a manual adjustment.

According to some embodiments of the present invention, there is provided a thoracic garment for positioning at least one EM transducer in proximity to a thoracic surface skin of a wearer. The thoracic garment comprises a thoracic garment having a piece of cloth having a low elasticity coefficient for covering at least an anterior thoracic piece and an EM transducer placement portion between about 2 centimeters (cm) and about 9 cm to a side of a central axis along the sternum of the wearer and between about 15 cm and about 9 cm below the upper end of the manubrium of a wearer wearing the thoracic garment and an arrangement of a plurality of straps connected to the thoracic garment and secured to one another at a support point located above the skin surface of the EM transducer placement portion;

wherein when the wearer wears the thoracic garment, at least one of the plurality of straps is placed across the thorax of the wearer, below armpits of the wearer, and another of the plurality of straps is placed across the shoulder of the wearer.

According to some embodiments of the present invention, there is provided a thoracic garment that comprises a thoracic garment, at least one EM transducer placement portion for positioning an EM transducer on a body of a wearer, at least one size adjusting mechanism for adjusting the size of the thoracic garment to the body of a wearer such that when worn an EM transducer positioned in the EM transducer placement portion will be placed at a predetermined location above the skin of the wearer, and a tightening mechanism for adjusting the pressure of the EM transducer on the body of the wearer. When a thoracic garment is worn by a wearer to whom it was fitted, and at least one EM transducer is placed in the at least one EM transducer placement portion and the tightening mechanism tightens the thoracic garment, the EM transducer is placed within ±2 cm from the predetermined location above the skin of the wearer for at least 50% of repeat wearing sessions without refitting.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings:

FIGS. 1A and 1B are posterior and anterior schematic illustrations of a thoracic garment, adapted to be worn with ease without the assistance of a caregiver, for positioning one or more EM transducer units above one or more thoracic skin surface area(s), according to some embodiments of the present invention;

FIG. 6C is a Y shape strap arrangement having a support point, according to some embodiments of the present invention;

FIG. 9 is a schematic drawing depicting an exemplary garment having pulling straps, according to some embodiments of the present invention.

DESCRIPTION OF EMBODIMENTS OF THE INVENTION

Figure 2A:
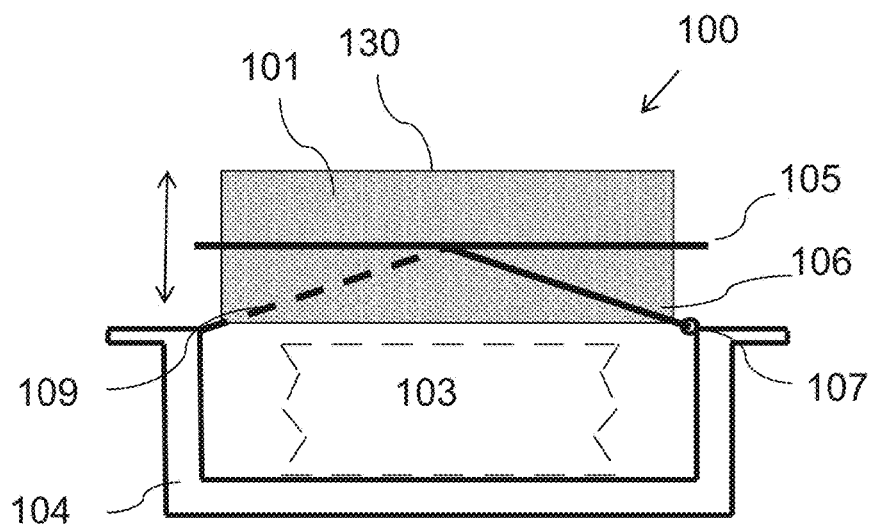
FIGS. 2A-2B are lateral and top schematic illustrations of an exemplary EM transducer unit 100, according to some embodiments of the present invention.

The present invention, in some embodiments thereof, relates to EM transducers positioning and, more particularly, but not exclusively, to a thoracic garment for positioning electromagnetic (EM) transducers and methods of using such a thoracic garment.

According to some embodiments of the present invention, there is provided a thoracic garment for bringing, in a repeatable manner, one or more EM transducers in contact with specific thoracic skin surface areas. Throughout this application, contact with skin surface may be taken to mean direct contact with the skin and/or indirect contact via one or more separating layers (e.g. though garment segments or garment fabrics and/or fabric or clothing worn above the specific skin surface areas). The thoracic garment has one or more EM transducer placement portions and one or more pressure applying elements for applying a pressure on at least one EM transducer secured in one of the EM transducer placement portions when the thoracic garment is worn by a wearer such that the EM transducer applies a respective pressure on a respective specific thoracic skin surface area. In some embodiments hereof, an "EM transducer" may be taken to mean a structure comprising one or more antennas or radiating elements for transmitting and/or intercepting EM energy and/or a group or array of the aforementioned.

As used herein, when the terms repeatable and repeatability are used with reference to placement, positioning and/or return to a position of an element, such as an EM transducer and/or a garment portion, they mean that the process is repeated with high precision of positioning so that the repeated positions of the element are close one to the other and/or with high accuracy of positioning so that the repeated positions of the element are close to a predetermined value. Optionally, the thoracic garment includes a set of straps, for example belts, bands, and/or thoracic garment pieces (also called garment portions) with fasteners, which are adjusted in a preliminary fitting session. It is noted that a garment piece may or may not be a physically separate from all other pieces. Rather in some embodiments two or more garment pieces are parts of a single continuous garment piece, while in other embodiments all garment pieces may be separate pieces connectable to each other by connectors. The preliminary fitting session adapts the thoracic garment to the body of the wearer so that the transducer placement portion(s) (and/or EM traducer(s) positioned therein) are above the skin surface at specific thoracic skin surface areas, and the garment is structured such that the transducer placement portion(s) (and/or EM traducer(s) positioned therein) are above the same specific thoracic skin surface areas when the thoracic garment is reworn a number of times after the preliminary fitting session ends.

According to some embodiments of the present invention, there is provided a thoracic garment and a controller which instructs pressure applying elements to increase pressure of EM transducers on skin surface areas after the thoracic garment is worn and to reduce the pressure before or when the wearer undresses. In such a manner, a physically impaired wearer (e.g. a person with diminished and/or limited dexterity) may self-dress with the thoracic garment, when it is relatively loose.

For example, undressing may be detected by a signal provided by the wearer (e.g. pressing a designated button or lever or any other user interface) or by the opening of a simple release fastener (e.g. a zipper or buckle). To this end an undressing detector may be used, for example an electric circuit that opens or closes when a simple release fastener is opened. Alternatively, the garment may be configured to prepare automatically for undressing, for example when a measurement session ends or a pre-set period expired or when a pressure and/or tilt sensor detects that a wearer sat up from a supine position, etc.

According to some embodiments of the present invention, there is provided a thoracic garment having EM transducer placement portions for positioning one or more pairs of EM transducers in opposing positions so the effective center for EM transmission and/or capturing of one EM transducer and/or a plurality of EM transducers (e.g. an array of transducers) is located above skin surface of an anterior thoracic skin surface area located between about 2 cm and about 9 cm (or even between about 4 cm and about 8 cm) to a side of a central axis along the sternum of the wearer and between about 2 cm and about 9 cm (or even between about 4 cm and about 8 cm) below the upper end of the manubrium of the wearer and the effective center for EM transmission and/or capturing of another EM transducer and/or another array of EM transducers is located above skin surface of a posterior thoracic skin surface area located between about 2 cm and about 9 cm (or even between about 4 cm and about 8 cm) to a side of a central axis along the spine of said wearer, and between about 12 cm and about 27 cm (or even between about 13 cm and about 23 cm, or even between about 15 cm and about 19 cm) below the upper end of the vertebra prominens of the wearer.

According to some embodiments of the present invention, there is provided a thoracic garment having EM transducer placement portions for positioning one or more pairs of EM transducers in opposing positions so that at least 30% of an effective EM capture and/or transmission area of one of the EM transducers is located above skin surface of an anterior thoracic skin surface area located between about 2 cm and about 9 cm (or even between about 4 cm and about 8 cm) to a side of a central axis along the sternum of the wearer and between about 2 cm and about 9 cm (or even between about 4 cm and about 8 cm) below the upper end of the manubrium of the wearer and at least 30% of an effective EM capture and/or transmission area of another EM transducer is located above skin surface of a posterior thoracic skin surface area located between about 2 cm and about 9 cm (or even between about 4 cm and about 8 cm) to a side of a central axis along the spine of said wearer, and between about 8 cm and about 30 cm (or even between about 14 cm and about 26 cm) below the upper end of the vertebra prominens of the wearer.

In some embodiments, the opposing EM transducers are both located on the right or left side of the body of the wearer. For example, if one EM transducer is located to one side (left or right) of a central axis along the sternum of the wearer (as seen from the front), an opposing EM transducer is located to an opposite side (i.e. right or left, respectively) of a central axis along the spine of said wearer (as seen from the back).

According to some embodiments of the present invention, there is provided an EM transducer unit for placement in a thoracic garment. The EM transducer unit has an anchoring surface, an EM transducer, and an extendable member having an adjustable length which changes a distance between the anchoring surface and the EM transducer.

According to some embodiments of the present invention, there is provided a thoracic garment having anterior and posterior thoracic pieces (also called portions), one or more EM transducer placement portions for securing one or more EM transducers, and adjustable straps each connects between lateral sides of the thoracic pieces and having an adjustable length to set the location of the EM transducer placement portion(s) in relation to a monitored intrabody region of the wearer of the thoracic garment.

According to some embodiments of the present invention, there is provided a thoracic garment having an arrangement of a plurality of straps connected to the thoracic garment and secured to one another at a support point, for example at a central support point located in front of said EM transducer placement portion so that when a wearer wears the thoracic garment one or more of the straps is placed across the thorax of the wearer, at a high position below his armpits and another of strap is placed across his shoulder.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Reference is now made to FIGS. 1A and 1B, which are anterior and posterior schematic illustrations of a thoracic garment 130, adapted to be worn with ease, optionally without the assistance of a caregiver, for positioning one or more EM transducer units 133 above one or more thoracic skin surface area(s), for example anterior and/or posterior thoracic skin surface(s) of a monitored wearer in a repeatable manner, according to some embodiments of the present invention. The thoracic garment 130 has one or more EM transducer placement portions 131, for example pockets, compartments, openings and/or attachments. Each EM transducer placement portion 131 is designed to host, for example to contain, at least one EM transducer unit 133. The EM transducer unit 133 is an EM transmission and/or reception unit which includes one or more EM transducer(s) 136, comprising for example antennas with or without a housing and/or associated electronics, which are connected to an EM controller 137, for example circuitry which controls EM energy emission and/or processing. It is noted that the EM transducer placement portion 131 may be a garment portion which includes any element capable of holding the EM transducer unit 133 at a predefined location, including for example an adhesive patch or any type of connector or mechanical attachment fixture matching a connector or mechanical attachment fixture on an EM transducer. The EM transducer unit(s) 133 may be attached to the EM transducer placement portion(s) 131, permanently or reversibly. For example, EM transducer unit (133) may be integral in a garment or garment portion (e.g. sewn or otherwise integrated in the portion). Accordingly the EM transducer placement portion(s) 131 of the thoracic garment 130 may be produced with the EM transducer unit(s) 133 and/or configured to have the EM transducer unit(s) 133 placed therein. The thoracic garment 130 and/or any portion thereof may comprise and/or be set to support additional sensors for example for gathering data related to the physical condition of the monitored subject.

The EM transducer unit 133 may be placed in a housing having a front surface shaped to be in contact with or conform to a curved portion of a human body in a standing, reclined, sitting and/or lying position, for example sitting on chair, lying in a bed, sitting on couch and/or standing.

The EM controller 137 may be part of the EM transducer unit 133 or external thereto. In some embodiments, a single controller 137 may be associated with a plurality of EM transducers (e.g. including a posterior and an anterior EM transducer). In some embodiments, the functions of controller 137 may be performed by a plurality of controllers. Each EM transducer unit 133 may have or be associated with at least one pressure applying element 132 for adjusting the pressure that is applied on the EM transducer(s) 136 when the thoracic garment 130 is worn by a wearer. The pressure applied on the EM transducer(s) 136 affects the pressure applied by the EM transducer unit 133 on a respective thoracic skin surface area. Optionally, each EM transducer unit 133 and/or the thoracic garment 130 includes or is connected to a pressure controller 135 which instructs how much pressure the pressure applying element 132 should apply on the respective thoracic skin surface. The pressure controller 135 may control a degree of pressure that is applied on the EM transducer 136 until the front surface thereof is in full surface contact (directly or indirectly, for example through fabric) with the respective thoracic skin surface to maintain a pressure on the skin during a sensing period, optionally at a level of pressure that does not cause undue discomfort to the wearer. The pressure controller 135 may be part of the EM transducer unit 133 or external thereto, and it may control the pressure of one or more EM transducer units.

It should be noted that though the EM transducer placement portion(s) 131 are described as part of the EM transducer unit(s) 133 at least some of them (e.g. a pressure applying element) may be independent therefrom. For example, the pressure applying element(s) 132 may be part of the thoracic garment, for example part of the EM transducer placement portion(s) 131, for example placed in an underarm region of the garment 130. In such embodiments, the transducer placement portion 131 may include an anchoring surface for supporting the pressure applying element 132 in action, for example a cup shaped housing as described below.

Optionally, the pressure applied on the body of a wearer compresses soft body tissues that cover the more rigid skeleton and/or muscular systems in the anterior and/or posterior thoracic skin surface areas. The pressure may increase the correspondence between the orientation of the transducer surface and the respective skeletal geometry, optionally as well as the distance between the EM transducer and a sensed intrabody region of the wearer in the dimension perpendicular to that structure's surface.

The pressure applying element 132 is optionally a linear actuator which creates linear motion that pushes the EM transducer 136 toward the body of the wearer, away from an anchoring surface of the transducer unit 133. The linear actuator may be electromechanical, mechanical, hydraulic and/or pneumatic and may be manually and/or automatically operated. For example, the pressure applying element 132 includes one or more inflatable components, optionally supported by a portion of the thoracic garment 130. Examples and further details for such structures are provided below. In use, the pressure applying element 132 displaces the EM transducer 136 so as to press it tightly against the subject's body. The degree of tightening of the thoracic garment 130 and/or inflation of a pressure applying element 132 or a portion thereof and/or displacement of the EM transducer unit may be controlled manually and/or automatically (e.g. by a mechanical pressure regulator set to automatically cut off and/or allow the flow of a fluid at a certain pressures) to a preset degree and/or based on feedback readings from a pressure sensor.

The pressure applying element 132 may reduce the distance between the surface of the EM transducer(s) 136 and a thoracic skin surface area, for example the skin surface in proximity to a monitored intrabody area (or increase the portion of the surface the EM transducer(s) 136 that is, directly or indirectly, in contact with the skin surface), and/or between the EM transducer(s) 136 and an intrabody area of interest under the skin by applying pressure on the EM transducer(s) 136, against pliable body tissue. This may increase the portion of EM energy, which is transmitted from the EM transducer(s) 136 and propagates into the intrabody area in a region of interest rather than travelling through unintended paths, for example on the skin.

The pressure applying element 132 may increase the repeatability of the positioning of the EM transducer(s). The pressure applying element 132 may assure that the EM transducer(s) 136 are in tight contact with the wearer's skin surface, directly or indirectly (e.g. through clothing), even if the thoracic garment in itself (without operation of the pressure applying element) is relatively loose. This may allow fitting the thoracic garment in a more comfortable manner, allowing a wearer to put it on or remove it with a relative ease. Tightening may be applied by pressure element(s) 132 at a direction essentially normal to the contact surface between a surface of an EM transducer and the body of a wearer.

Optionally, the pressure applying element 132 applies force divided essentially equally across the surface of the EM transducer(s) 136 and/or centered on the EM transducer(s)'s or the antenna(s)'s geometric center such that the entire surface of the EM transducer(s) or at least 90% or at least 75% thereof is in contact with a subject's body (directly or indirectly) and/or the EM transducer 136 does not easily tilt away from a substantially normal orientation in relation to the skeletal and/or muscular structure of the body under the skin surface at the area of contact. This may be of importance especially when an EM transducer 136 has a relatively large footprint, for example a cross-section measuring 4 cm or more or 6 cm or more or even 8 cm or more in at least one direction, but may be useful also for smaller footprints.

Optionally, the pressure applying element 132 includes a tilting mechanism which allow the EM transducer(s) 136 to tilt in response to the wearer's body structure and composition and to repeatedly reach approximately the same position at a plurality of measurement sessions once pressure is applied, for example as described below.

Figure 2B:
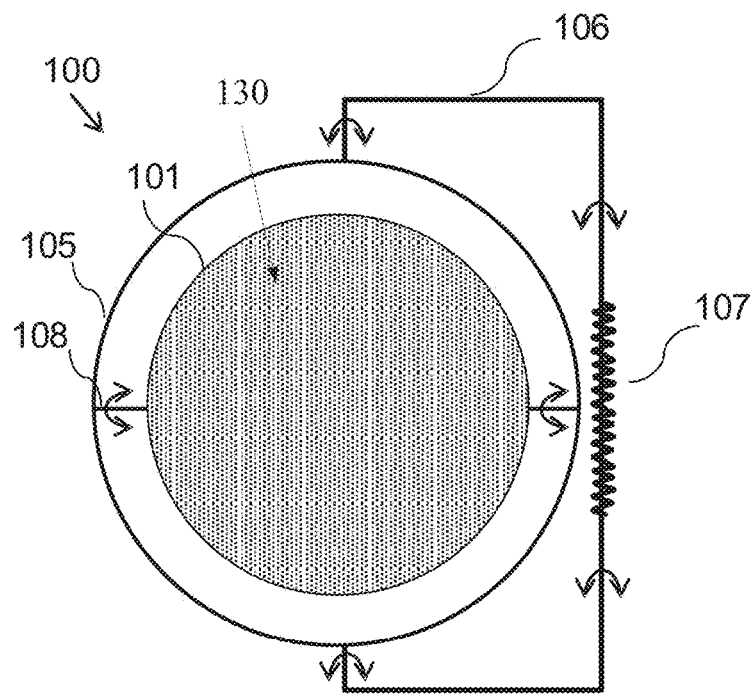

For example, reference is now also made to FIGS. 2A-2B, which are lateral and top schematic illustrations of an exemplary EM transducer unit 100, according to some embodiments of the present invention. FIG. 2A depicts a lateral view of an exemplary EM transducer unit 100 having an EM transducer 101 with a frontal surface 130 positioned slightly above an opening of a pressure applying element which includes a cup shaped housing 104 that functions as an anchoring mechanism. The cup shaped housing 104 is shown in an exemplary cross section, but may be shaped for example as a box, a cube, a dome, a cone and/or a pyramid. The housing 104 may comprise any material which is durable and/or non-elastic enough and/or rigid enough to provide support to EM transducer(s) 101 and to allow pressure to be applied to the EM transducer(s) during operation such that the frontal surface 130 is displaced and move away from the bottom of the housing toward the thoracic skin surface area.

Optionally, the housing 104 is made of or at least partially coated with an EM manipulating material, for example an EM conductive or absorbing material. The pressure applying element further includes an extendable member 103 positioned in the housing 104 to push the EM transducer 101. Extendable member 103 may be for example a pneumatic linear actuator or an inflatable member that may be inflated by a fluid, be it liquid or gas. Extendible member 103 may include for example, under and/or around the EM transducer, a spring and/or a piston operated by a motor.

In use, the EM transducer unit 100 is positioned with the frontal surface 130 facing a skin surface area of a wearer. Optionally, the EM transducer unit 100 is secured to the body of the wearer by one or more straps and/or an anterior and/or posterior thoracic garment 130. The straps and/or posterior thoracic garment 130 fixes the housing 104 such that upon extension of the extendible member 103, the EM transducer 101 moves in the direction of the subject's body thereby coming to tight contact between the frontal surface 130 and the skin surface of the wearer.

FIG. 2B depicts a top view of the EM transducer unit 100, showing an exemplary tilt mechanism having a gimbal arrangement (105, 106, also shown from lateral view in FIG.

2A) attached to an EM transducer 101. The gimbal arrangement ring 105 is connected to the EM transducer 101 by axel 108, allowing the EM transducer 101 to tilt around the axel. The gimbal arrangement ring 105 is attached to frame 106 such that the EM transducer 101 may rotate around the axis formed by the frame 106 where contacting the EM transducer 101.

As seen in FIG. 2A, frame 106 is hingedly connected to housing 104 such that the edge of the frame that is not attached to the housing may move upwards and allow EM transducer(s) 101 to move away from housing 104 as extendible element 103 extends. Optionally, arm 109 is hingedly connected to housing 104 through a first edge of the arm on one side and a second edge is slidably connected to frame 106. When EM transducer 101 is pushed away from housing 104, the second edge of arm 109 moves upwards, slides along an arm of frame 106 to move EM transducer 101 essentially vertically away from housing 104.

In some embodiments, the EM transducer 101 may be displaced vertically a distance of 2-6 cm or 3-5 cm. When extendible element 103 retracts, for example when it is deflated, EM transducer 101 is free to return into housing 104, for example by a counter pressure from the body of the wearer. This may be facilitated by exerting force in essentially the same direction, for example by spring 107.

Figure 3:
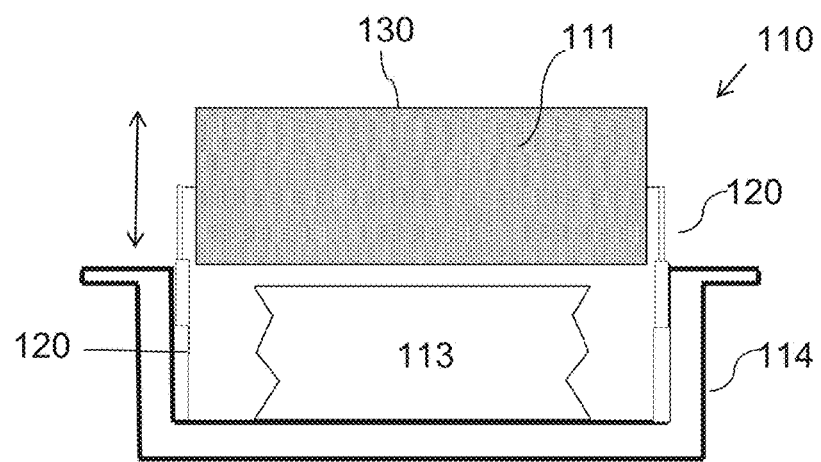
FIG. 3 is a lateral view of an alternative EM transducer unit, according to some embodiments of the present invention.

FIG. 3 depicts a lateral view of an alternative EM transducer unit 110 where an EM transducer 111 is held in housing 114 and pushed away from the bottom of the housing by an extendible element 113. In this example, the EM transducer 111 is anchored to the bottom of the housing 114 using a number of telescopic elements 120. When the EM transducer 111 is pushed away from the housing 114, telescopic elements 120 extend, holding it in position during movement. Once extendible element 113 retracts telescopic elements 120 retract and allow the EM transducer 111 to move toward the bottom of the housing 114 or even pull it in this direction.

Figure 4A:
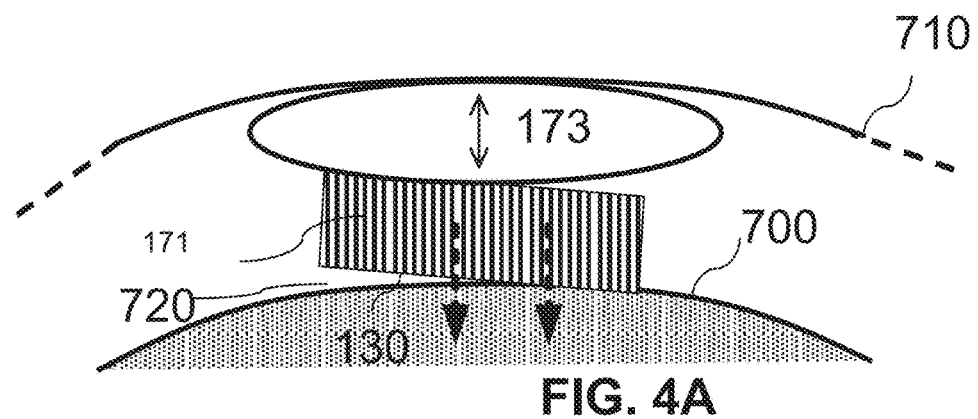
FIGS. 4A and 4B are schematic cross sections of an EM transducer unit having an inflatable pressure applying element, according to some embodiments of the present invention.
Figure 4B:
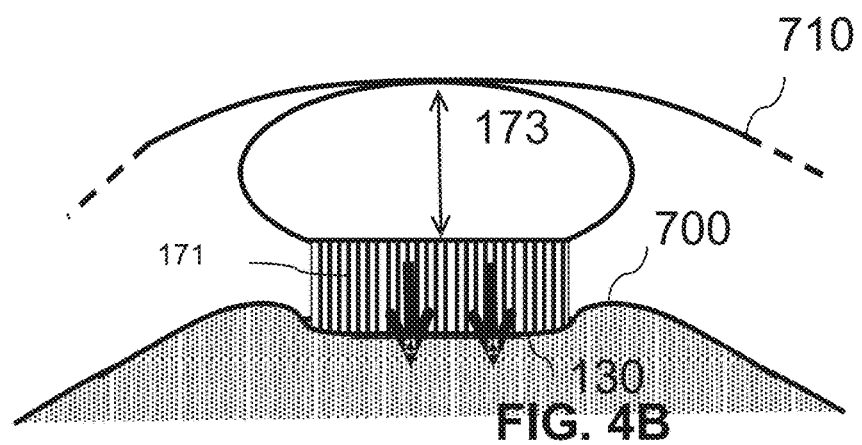

Reference is now made to FIGS. 4A and 4B which are schematic cross sections of an EM transducer unit 171, placed between a thoracic garment piece 710 and a patient body surface 700, directly or indirectly (for example above a piece of an undershirt or any other garment or fabric that is worn on the upper body or is a part of the garment), according to some embodiments of the present invention. In FIGS. 4A and 4B, the extendible member 173 is an inflatable element positioned between garment piece 710 and EM transducer 171 that is respectively depicted in partly deflated and inflated states. As used herein inflating and deflating are performed by flowing a fluid (liquid and/or gas). While the garment is fitted to some degree of tightness to the subject and hence exerts a low pressure on body surface, for example a in the direction depicted by dashed arrows, it is loose enough to allow the EM transducer surface 130 to tilt with respect to body surface 700. The tilt forms a gap 720 between EM transducer surface 130 and the body surface 700. As extendible member 173 and the EM transducer 171 are sandwiched between a relatively non-elastic garment portion 710 and the patient's body, extension of extendible member 103 caused EM transducer 171 to apply a higher degree of pressure on the subject's body surface 700, depicted by bold line arrows in FIG. 4B. Since the subject's body comprises pliable tissue(s) at the area shown, the body part compresses slightly under the pressure and surface 130 of EM transducer 171 is brought to full surface contact with body surface 700. Such an arrangement as shown in FIGS. 4A and 4B (including an EM traducer unit 171 and extendible member 173) may in some embodiments be sewn into the garment, with a layer of material (e.g. a fabric or cloth) placed under EM transducer 171 (not shown). Thus, when in use, the layer of material will come between EM transducer surface 130 and the body surface 700.

Optionally, the above mentioned pressure controller (not shown) controls the degree of displacement of the EM transducer 101, 111 or 171 from within its housing or from its support (e.g. garment piece 710) and towards the body and/or the pressure exerted by the EM transducer(s) mechanism on the subject and/or the pressure exerted on the EM transducer(s). The EM transducer surface 130 may be pushed from a resting position in a housing and towards a subject's body by 0.5 or more centimeters (cm). For example, this may be between 0 cm and 7 cm or more, for example between 3 cm and 5 cm or more.

Optionally, the pressure level applied on the EM transducer 101, 111 or 171 may be between 100 millibar (mbar) and 600 mbar, for example between 200 mbar and 400 mbar or about 300 mbar within inflatable member 173 or and/or between 0.01 $Kg/cm^2$ and 0.3 $Kg/cm^2$ on the subject's body. The degree of pressure may be set to be the same for a plurality of measurements to ensure repeatability of the pressure and/or comparability of measurements taken at different times. This may be controlled for example by a gauge, a pressure sensor, to provide feedback control for a pneumatic or hydraulic pump which pumps fluid into the inflatable member 173 or 113 or 103 and/or by use of a displacement sensor. Optionally, pressure may be controlled manually. Optionally, the outcome of the gauge, a pressure and/or a displacement degree, is displayed to allow a manual pressure adjustment. Alternatively or additionally, it may be desired to take EM measurements at a plurality of different pressure/displacement settings.

Additional mechanisms may be used for retracting an EM transducer form a position where it applies pressure on a wearer's body. For example, in some embodiments, an EM transducer may be retracted by releasing pressure from an inflatable member 103, 113 or 173 and allowing for gravity and/or a retracting motion of the extendible member or a portion thereof to pull the EM transducer.

Additionally or alternatively one or more springs and/or elastic components that are attached, directly or indirectly to the EM transducer and an anchoring position can be used (for example spring 107 as described above). When an extendible member extends and displaces the EM transducer, the spring and/elastic components extend as well. Once the extendible member retracts or reduces the pressure applied on the EM transducer, the spring and/elastic components snap back to position, pulling the EM transducer with them.

In order to reduce the chance of the EM element displacing once an inflatable member is deflated (e.g. during undressing and/or redressing), a mechanism may be used to manually or automatically lock the EM transducer in place. This function may be provided at least partly, the aforementioned spring and/or elastic components. Additionally or alternatively, to reduce unintentional inflation of an inflatable member (even if partial) a valve in the inflatable member that might allow fluid into the inflatable member is shut, thereby preventing fluid from flowing back into the inflatable member (e.g. air from the environment).

Reference is now made, once again, to FIGS. 1A and 1B. The thoracic garment 130 may be adapted to be worn continuously and/or intermediately to perform continuous and/or intermittent measurements, for bedridden and/or ambulatory wearers. The thoracic garment 130 may be provided in various sizes to fit wearers having different body shapes and measures (e.g. waist circumference and thorax length). In addition, the thoracic garment 130 may include one or more fasteners to allow fitting to a curves and sizes of a specific subject. As further described below, these one or more fasteners are lockable to avoid a change in the relative location of the EM transducer placement portion 131 in relation to the garment (and consequently thoracic skin surface areas), which change may be caused by the dressing and undressing of the thoracic garment 130 or by misuse.

The thoracic garment 130 may be used for one or more EM transducer units 133 which are used for the assessment of dielectric related properties of one or more organ(s) and/or tissue(s) based measurements and/or calculation of one or more biological parameters, for example lung fluid content. According to some embodiments of the present invention, the garment allows placing EM transducer units with a high repeatability or high return to position of the EM transducer with respect to the wearer's body (i.e. at a high accuracy and/or precision), for example as described below.

The biological parameters may be assessed based on measurements of EM signal(s) and/or field(s) and/or energy affected by the dielectric related properties of body or a part thereof, optionally with combination of other data from additional sensors. Examples of additional sensors include one or more sensors, optionally integrated or attached to the garment, configured for gathering data related to a physical condition of a monitored subject, for example electrocardiogram (ECG) sensors, electromyogram (EMG) sensors, ultrasound transducer(s), blood pressure sensor(s), optical blood saturation detector(s), pulse oximeter(s), activity sensor(s), such as accelerometer(s), tiltmeter(s), microphone(s), capnometer(s), and/or coagulometer(s). In this context, a physical condition means data related to the physical activity, vital signs, biological parameters, and/or any other medical and/or biological information which is indicative of the wearer wellness and/or fitness of the monitored wearer.

As used herein, a dielectric related property of a specific volume which includes one or more organs and/or tissues may describe or relate to an interaction with EM energy and may be represented by a frequency dependent complex number describing the electrical permittivity and/or material conductivity. For example, dielectric related property may be an electric permittivity coefficient, conductivity coefficient and/or a magnetic permeability coefficient of a material, optionally composite, within a specific volume. Such a dielectric related property may be affected for example by a presence or distribution of fluid, concentration of substances, such as salts, glucose, in the fluid in the internal tissue and/or organ, the ratio of fibrotic tissue, a concentration of inflammatory substance in the fluid in the internal tissue and/or organ and physical configuration of organs or tissues of different properties in the volume measured.

Measurements of dielectric related properties may be conducted by transmitting EM energy and/or EM signal and/or intercepting it using the EM transducer unit(s) 133. Intercepted EM energy and derived electrical signals may be analyzed using one or more signal properties using known signal analysis methods. For example time domain or frequency domain analysis methods, for example one or more of amplitude, phase, signal morphology feature extraction, and/or group delay analyzed over different bands of frequencies (potentially between 100 MHZ and 5 GHz or any portion thereof).

Optionally, the EM controller 137 or a remote processor (not shown) calculates a dielectric related change or a dielectric property related change by analyzing changes in the intercepted EM energy during a number of EM radiation sessions held during a monitoring period. Communication between system components (including for example one or more of EM transducer unit(s), controller(s) and/or remote processor(s)) may be performed in any method known in the art, including by wireless communication.

Non-limiting examples for using RF and MW radiation for monitoring and diagnosing body tissues, as well as examples for effects of internal physiological activities, effects of external physiological activities and handling of movement effects and other methods and/or apparatuses, that may be useful in conjunction with the following, are described in International Patent Applications published as WO2009/031149, and WO2009/031150 filed on Sep. 4, 2008, International Patent Application published as WO2010/100649 filed Mar. 4, 2010, and International Patent Application published as WO2011/141915 filed May 12, 2011, and International Patent Application No. PCT/IL2011/050003 filed Nov. 3, 2011 and US patent applications published as US 2010-0056907 (filed Aug. 20, 2009) and US 2011-0025295 (filed Jul. 30, 2010) all of which are incorporated herein by reference in their entirety.

According to some embodiments of the present invention, the thoracic garment 130 is sized and shaped so that the EM transducer placement portions 131 thereof are located, when the garment 130 is worn, in a manner that 30% or more of an effective EM capture and/or transmission area of the EM transducer unit is located above skin surface of an anterior thoracic skin surface area located between about 2 centimeters (cm) and about 9 cm (or even between about 4 cm and about 8 cm) to a side of a central axis along the sternum of the wearer 10 and between about 2 cm and about 9 cm (or even between about 4 cm and about 8 cm) below the upper end of the manubrium of the wearer 10. Additionally or alternatively 30% or more of an effective EM capture and/or transmission area of the EM transducer unit is located above skin surface of a posterior thoracic skin surface area located between about 2 cm and about 9 cm (or even between about 4 cm and about 8 cm) to a side of a central axis along the spine of the wearer 10, and between about 8 cm and about 30 cm (or even between about 14 cm and about 26 cm) below the upper end of the vertebra prominens of the wearer 10.

Figure 5A:
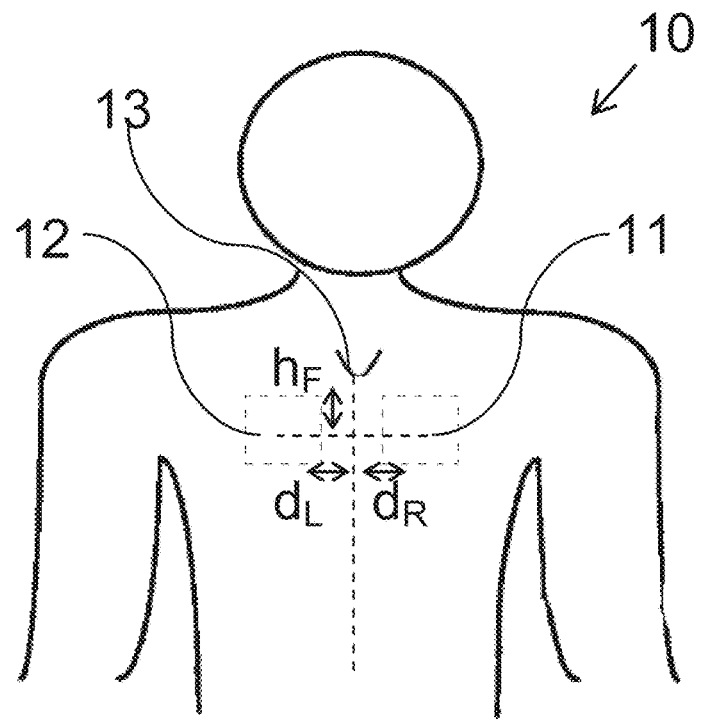
FIGS. 5A and 5B are schematic anterior and posterior illustrations of an exemplary wearer and exemplary anterior and posterior thoracic skin surface areas, according to some embodiments of the presented invention.
Figure 5B:
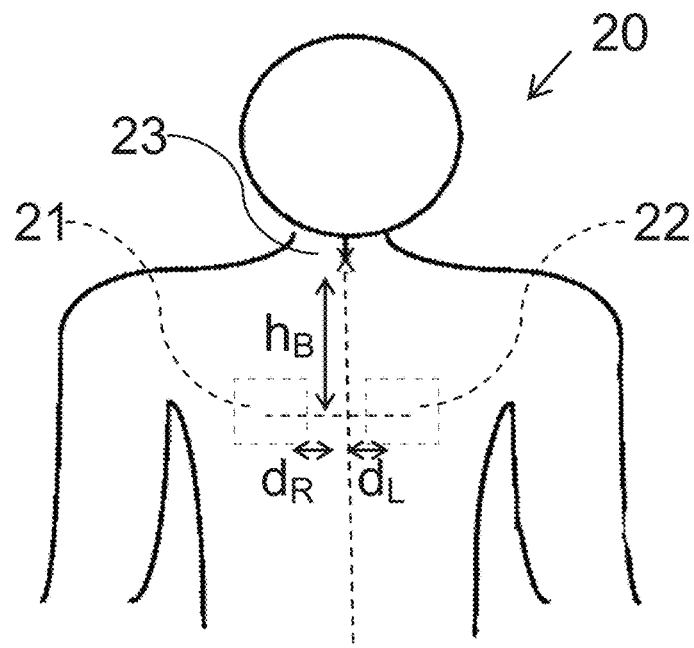

For example, reference is now made to FIGS. 5A and 5B which are schematic anterior and posterior illustrations of an exemplary wearer 10 or 20 and his exemplary anterior and posterior thoracic skin surface areas for monitoring and/or detecting a dielectric related property in or in proximity to a lung, according to some embodiments of the presented invention. Optionally, a single EM transducer unit is placed in one of the thoracic skin surface areas. Optionally, one member of a pair of EM transducer units is placed in one anterior thoracic skin surface area and another is placed in an opposing posterior thoracic skin surface area. Optionally, a number of EM transducer units are placed in a number of anterior and/or posterior thoracic skin surface areas. The thoracic garment which is described herein includes one or more EM transducer placement portions which are described to be placed above the skin surface of any of the above described thoracic skin surface areas. These EM transducer placement portions may be used for positioning any EM transducer unit, for example with or without the aforementioned pressure applying elements.

In FIG. 5A, two optional anterior thoracic skin surface areas, numerated as 11 and 12, are depicted on the chest of a wearer 10. These positions may be characterized relative to the wearer's jugular notch 13 at the top of the manubrium.

The anterior thoracic skin surface area is selected such that an EM transducer unit is at a distance $h_F$ vertically below notch 13, and a distance $d_R$ or $d_L$ to the right or left, respectively, of notch 13. Each of areas 11 and 12 schematically depicts an area above the skin of a wearer 10 where, in some embodiments, at least 30% of an effective EM capture and/or transmission area of one of the EM transducers or of a group of EM transducers (e.g. an array of EM transducers) is located. Additionally or alternatively, each of areas 11 and 12 schematically depicts an area above the skin of a wearer 10 in which an effective center EM transmission and/or capturing of one EM transducer and/or a plurality of EM transducers (e.g. an array of EM transducers) is located. Examples for measurements defining areas 11 and 12 are disclosed in Table 1.

TABLE 1

| $h_B$ (cm) | $d_R$, $d_L$, $h_F$ (cm) | Area significance |
|---|---|---|
| 12-25 or 13-23, or 15-19 or 17, 18, 19 or 20 | 2-9 or 4-8 or 5, 6, 7 or 8 cm | Effective center |
| 8-30 or 14-26 | 2-9 or 3-7 | 30% of transmission |

In the Table 1, where $d_R$, $d_L$, $h_F$ and $h_B$ denote a specific distance (and not a range) they may be selected to vary by 1-3 cm (or define an area based on the measurement ±1, 2 or 3 cm), for example to match persons with extreme body size measures. The table measurements are of an exemplary subject sitting upright and/or standing. It should be noted that the EM transducer unit may be used to intercept EM energy in various positions, including standing, sitting or reclined at different angles, for example between 10° and 30° in relation to above a bed surface plane.

In some embodiments, the garment is fitted such that, alternatively or additionally, the effective center of an EM transducer placed within the EM transducer placement portion is located in area 11 and/or in area 12. The effective center of an EM transducer or of an antenna within the EM transducer or of an array of antennas or EM transducers may be taken to mean the position where the boresight (as measured in free space) or the center of the main beam of the EM transducer (or antenna or array), in the direction of the body of the wearer, would intersect the skin of a wearer.

FIG. 5B depicts two optional posterior thoracic skin surface areas 21, 22 on the body of exemplary wearer 20. These positions may be defined respective cervical vertebra C7 (vertebra prominens; hereinafter vertebra 23) of the wearer 20. Each of areas 21 and 22 schematically depicts an area above the skin of a wearer 20 where, in some embodiments, at least 30% of an effective EM capture and/or transmission area of one of the EM transducers and/or a plurality of EM transducers (e.g. an array of transducers) is located. Additionally or alternatively, each of areas 11 and 12 schematically depicts an area above the skin of a wearer 10 in which an effective center for EM transmission and/or capturing of one EM transducer and/or a plurality of EM transducers (e.g. an array of transducers) is located. Examples for measurements defining areas 21 and 22 are disclosed in Table 1.

In some embodiments, the garment is fitted such that, alternatively or additionally, the effective center of an EM transducer placed within the EM transducer placement portion is located in area 21 and/or in area 22.

In some embodiments, the garment is fitted such that, alternatively or additionally, the effective center of at least one EM transducer placed within the EM transducer placement portion is located in area 21 or in area 22 and the effective center of at least one other EM transducer placed within an EM transducer placement portion is located in area 11 or in area 12.

It should be noted that while the above thoracic skin surface areas were defined respective the jugular notch or cervical vertebra C7, any other methodology of finding the same thoracic skin surface areas on a body of a subject may be employed. For example, this may be performed with respect to one or more other skeletal features.

According to some embodiments of the present invention, there is provided a set and/or a kit of thoracic garments, each as defined above and sized and shaped to fit one of a plurality of body shapes and/or sizes, for example shirt sizes. This set and/or kit may be used for adapting a suitable thoracic garment to a patient. A thoracic garment, which may be reusable and/or adapted for a single patient, may be sold and/or let upon demand.

Figure 10:
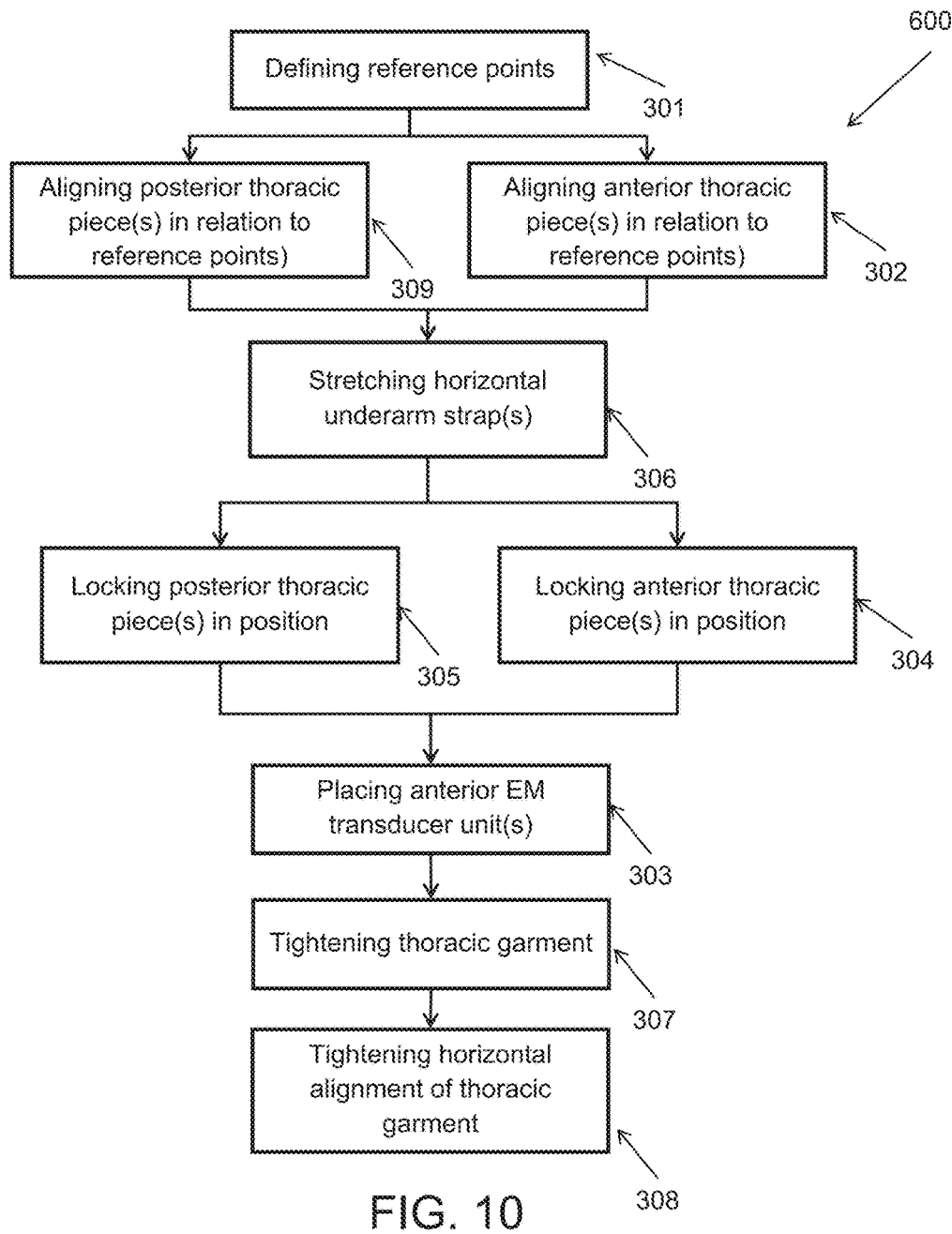
FIG. 10 is a flowchart of an exemplary preliminary fitting session, according to some embodiments of the present invention.

Optionally, the garment with any of the above EM transducer placement portions 131 is set to be adapted to the body of a wearer in a preliminary fitting session and then locked in position. The fitting is optionally performed by adjusting the length of a plurality of straps which are attached to posterior, anterior, and optionally shoulder pieces of the thoracic garment 130. As used herein, a strap is an element having an adjustable length and/or elasticity which is attached to at least two pieces of a garment, or is comprised in at least one piece of a garment and attached to another piece, for example a belt, one or more fasteners, a buckle and/or the like. In some cases, an element is considered to have an adjustable length by virtue of having a plurality of alternative positions to overlap with another part of the garment (e.g. different fastening positions of a hook and loop element), thereby changing a length of a garment portion that is determined by the element. Optionally, some segments of the thoracic garment 130 having a surface allowing the attachment of hook and loop fasteners thereto. These segments, together with the respective hook and loop fasteners, may be referred to herein as straps. An exemplary preliminary fitting session is depicted in FIG. 10 and described with reference thereto.

Optionally, in order to maintain the EM transducer unit(s) 133 firmly in place in relation to the thoracic skin surface areas, the thoracic garment 130 is made of a relatively non elastic material (optionally a relatively rigid material) which is not stretched by bodily movements.

Optionally, the thoracic garment 130 includes at least two non-elastic (optionally rigid) pieces, a shoulder piece and an underarm piece, for example in the form of one or more straps, for example harnesses, and/or in the form of a garment piece, for example a structured non-elastic portion of the fabric shaped to cover a portion of the wearer's neck and/or shoulders and/or a horizontal portion of the upper thorax). Optionally the at least two non-elastic pieces, a shoulder piece and an underarm piece, are provided as an integral part of the garment, optionally one or more of them is visibly indistinguishable from the rest of the garment surface and/or provided as an internal layer in the garment being part of a bottommost or a middle layer. Garment pieces may be included in a vest, a shirt, a coat, a pullover, sleeveless or not, and/or the like. A garment component may be regarded as rigid and/or non-elastic if it is sufficiently deformation and/or stretch-resistant to maintain the garment shape so that the EM transducer placement portions remains in place in relation to the thoracic skin surface areas during wearing and between at least 5 or at least 10 wearing sessions.

Optionally, the shoulder piece (and/or the underarm piece) includes an EM transducer placement portion to position one or more EM transducer units above the skin surface of a posterior and/or anterior thoracic skin surface area. The shoulder piece may be supported around the shoulder and/or around the neck region to fix vertically the EM transducer placement portions of the garment with respect to the shoulder or neckline. The underarm piece may be placed tightly under the armpit to fix vertically the EM transducer placement portions of the garment. Alternatively or additionally, the underarm portion may also serve for tightening and/or horizontally fixing the position of the EM transducer unit. Additional components may also serve one or more of the aforementioned purposes. The underarm portion may span the circumference of the thorax horizontally and comprise one or more straps and/or other garment portions and fabrics.

The aforementioned low elasticity and/or rigidity, may cause an EM transducer unit and/or additional sensor associated therewith to remain essentially stationary with respect to the thoracic skin surface area(s) and to be repeatedly placed at the same location and/or to assure the thoracic garment maintains its shape and size when it is redressed. The garment portions need not be too rigid so as to allow some wearer movement and comfort with the EM transducer unit being capable of being in contact with the wearer's body (even if through a layer of clothing).

In some embodiments, the thoracic garment 130 is intended for use by a feeble and/or physically impaired subject (e.g. a person with diminished and/or limited dexterity). In such embodiment, the fitting tightness, the degree of elasticity, the degree of rigidity and/or garment structure allow self-dressing and undressing by the subject, possibly without assistance from a caregiver.

Optionally, the thoracic garment 80 is reusable. Such a thoracic garment 80 is shaped and sized to have EM transducer units returned to position at a high accuracy and/or precision after the thoracic garment 80 is refitted to one patient and then to another.

Figure 6B:
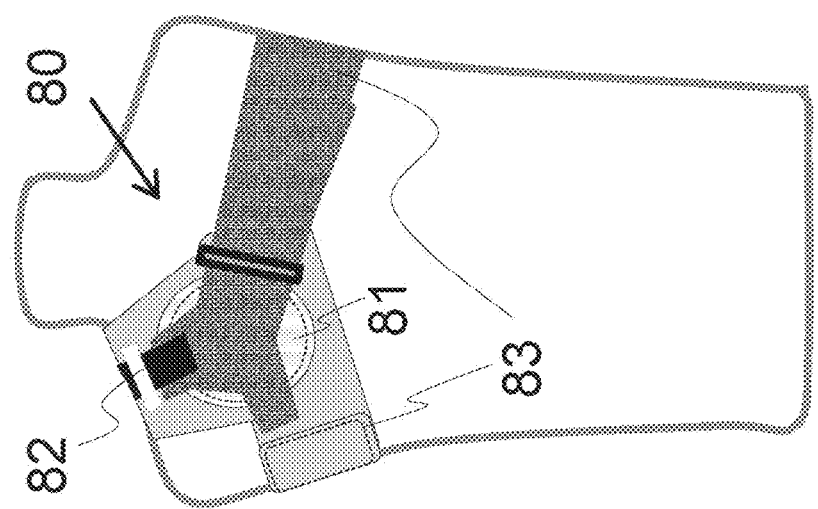
FIGS. 6A-6B are, respectively, posterior and anterior schematic drawings of an exemplary thoracic garment having a number of EM transducer placement portions located to be above the skin surface of an anterior thoracic target area and above the skin surface of a posterior thoracic target area, according to some embodiments of the present invention.
Figure 6A:
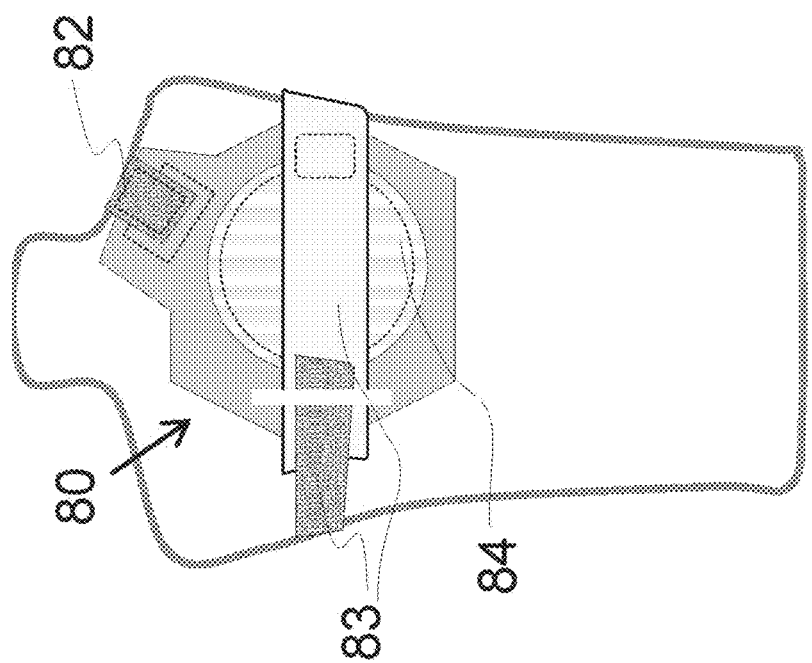

Reference is now made to FIGS. 6A-6B, which are posterior and anterior schematic illustrations of an exemplary thoracic garment 80 having a number of EM transducer placement portions 81, 84 located to be above the skin surface of an anterior thoracic target area and above the skin surface of a posterior thoracic target area, respectively. The thoracic garment 80 includes harnesses which are essentially horizontal to the body (harness 83) and essentially vertical to the body (harness 82). The horizontal harness, which comprises a number of strap portions, binds around the chest of a subject and is placed diagonally under the arm of a subject at an angle from a lower point on the back to a higher point on the chest at a location adjacent a chest EM transducer unit structure 81. The vertical harness, a shoulder strap, fixes the EM transducer unit vertically. The harnesses support the EM transducer units in portions 81, 84 and comprises fastening members (unseen hook and loop fasteners in overlapping portions of the harnesses in the instant example) to allow fitting to specific wearers.

The straps may be a Y shape strap arrangement extending below and above one shoulder and below another shoulder. The Y shape strap arrangement has a support point located above or near the EM transducer placement portion (or the EM transducer when positioned in the garment) above the armpit line, for example see FIG. 6C. Optionally, the thoracic garment 80 includes locking members to allow removing and redressing without need for readjustment (not shown).

The flexibility of the thoracic garment 80 allows the wearer to breathe easily, to move in comfort without dislocation of EM transducer units, to maintain the EM transducer units in place during separate wearing sessions while the garment is laid aside.

Reference is now made to FIGS. 7A-7E, which are respectively anterior, posterior, right and left lateral lining sides, and flap schematic illustrations of an exemplary thoracic garment 30 having a number of EM transducer placement portions 33, 42 to be located (when worn) above the skin surface of an anterior thoracic target area and above the skin surface of a posterior thoracic target area, respectively. The thoracic garment 30 includes a shoulder piece 31 that comprises frontal fastening members 311 bounded to an anterior garment piece 32 at a plurality of alternative vertical positions. This allows selecting at least the vertical position of EM transducer unit 339 (not seen; location within EM transducer placement portion 33 marked with dashed arrow in FIG. 7A) by fixing anterior piece (also called anterior portion) 32 at a desired longitudinal location respective shoulder piece 31. It should be noted that exemplary thoracic garment 30 is designed to monitor an intrabody lung tissue by intercepting EM energy from the right side of the body of the wearer. A mirror image thoracic garment with similar EM transducer placement portions 33, 42 on the left side may be similarly created. Also thoracic garments with EM transducer placement portions on both left and right sides of the chest and back may be similarly created.

Essentially the same garment structure may be manufactured having different antenna placement portions if it is to be used to position EM transducers at other (additional or alternative) places with respect to the wearer's body. For example, one or more EM transducers may be positioned on the sternum of the wearer. For example, one or more EM transducers may be positions at a location allowing the transmission and/or reception of EM energy passing through and/or reflected from the heart of a wearer. It should be noted that exemplary EM transducer placement portions shown in FIG. 7A-7E are shown to encase EM transducer units in a hardened shielded structure. The EM transducer units include pressure applying elements 132 (in this example pneumatic) to further attach the EM transducer units to the skin surface of the wearer. Optionally, the shoulder piece 31 comprises posterior fastening members 312 that bind to a posterior portion 43 at a plurality of alternative vertical positions. This allows selecting the vertical position of window 422 by fixing posterior portion 43 at least vertically at a desired longitudinal location respective shoulder piece 31.

Optionally, one or more of the garment pieces (e.g. anterior garment piece 32 and/or posterior portion 43) comprise detachable portions, allowing the garment to be worn in two or more configurations. Optionally a garment may be produced having a plurality of alternative garment pieces (e.g. a plurality of alternative anterior garment piece 32 and/or a plurality of alternative posterior portion 43), allowing the garment to be combined in two or more configurations. In such cases, in one configuration the garment may cover a skin surface area of the wearer's body being larger than the skin surface area of the wearer's body that is covered by the same garment with a different configuration (e.g. detachable portion removed or a different alternative portion used). In some embodiments, the different configurations are intended to provide ease of use under varying configurations. For example—when the garment is at a configuration capable of covering a larger skin surface area, it may be easier for a wearer to self-dress and/or undress (for example, when used at home). Conversely, when the garment is at a configuration capable of covering a smaller skin surface area, it may be easier for a caregiver to dress and/or undress a wearer (for example in a hospital setting).

Figure 7A:
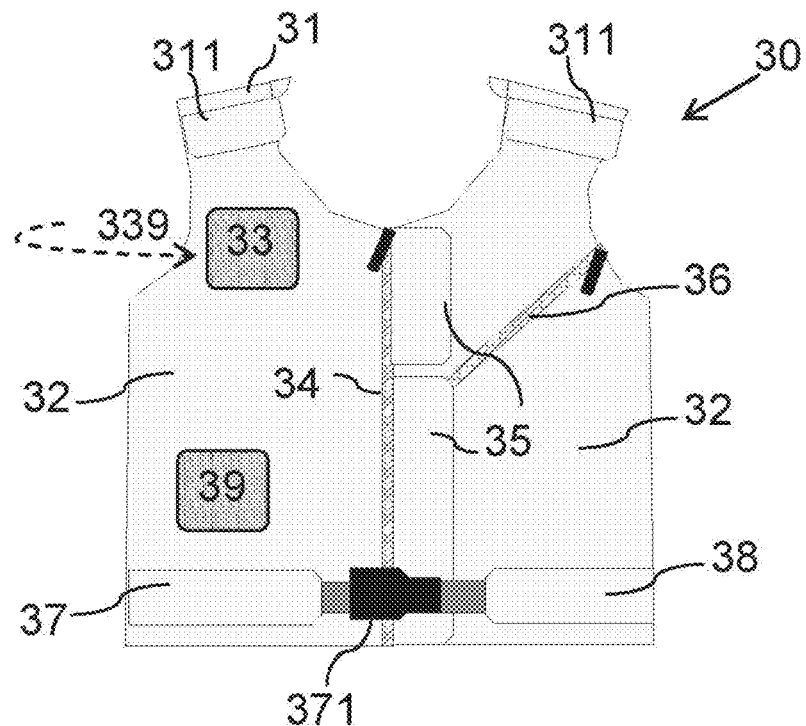
FIGS. 7A-7E are schematic drawings respectively exemplifying anterior and posterior views of a thoracic garment having a number of EM transducer placement portions, right lining and left lining side views of a garment, and an opened flap covering a posterior EM transducer unit, according to some embodiments of the present invention.
Figure 7B:
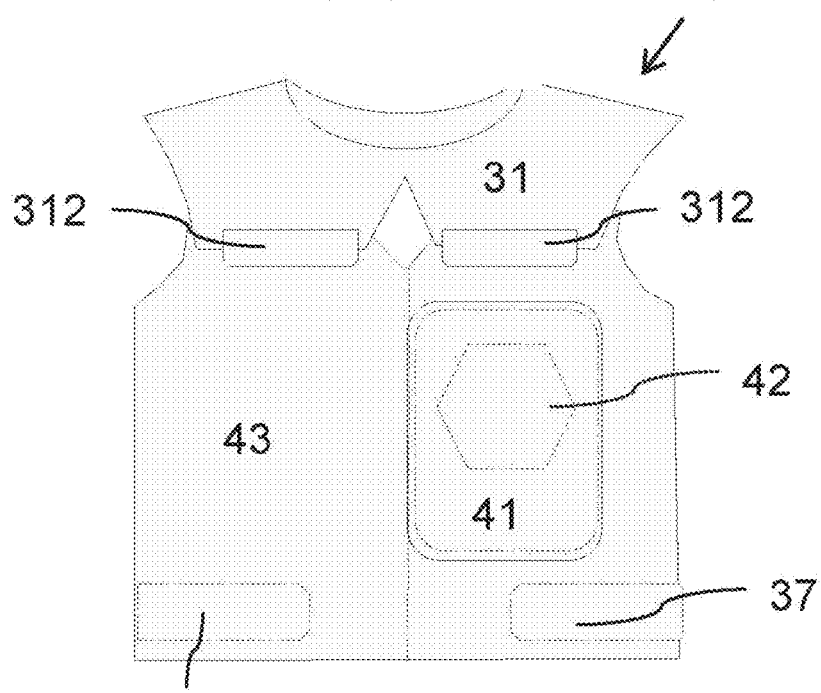
Figure 7C:
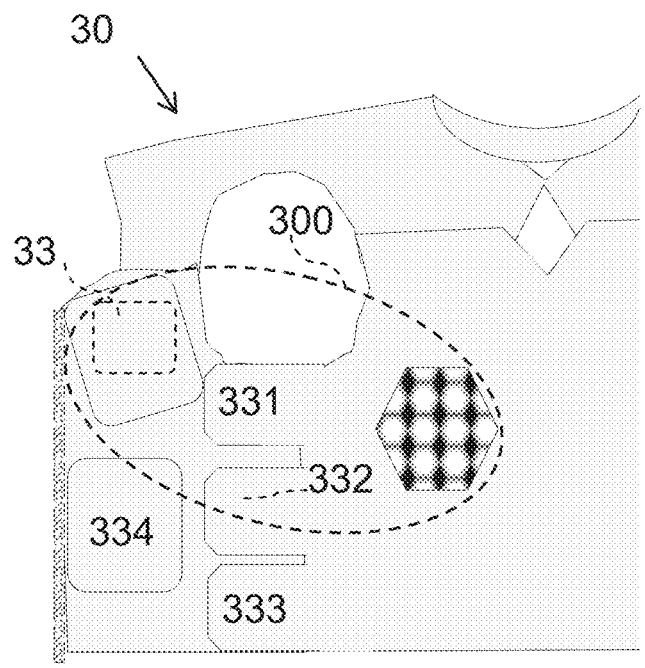
Figure 7D:
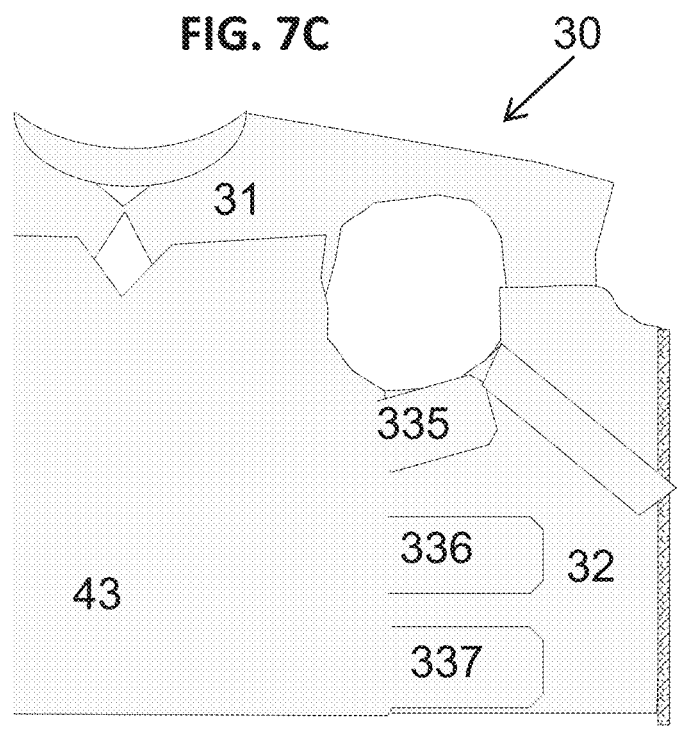

As depicted in FIGS. 7C and 7D, posterior portion 42 comprises horizontal straps 331, 332, 333, 335, 336 and 337 which may be bound to anterior piece 31 at any of a plurality of horizontal positions. This allows selecting and/or fixing the horizontal positions of EM transducer placement portion 33 and EM transducer portion 42 (or window 422) by selecting the fastening the straps at respective pluralities of horizontal locations on anterior piece 32. This may allow, additionally or alternatively, fitting the garment to the contour of a subject by selecting the location separately for each strap or pair of straps, see for example 331 and 335, 332 and 336, and 333 and 337 in FIGS. 7C and 7D. This in turn may improve the precision of returning the EM transducer unit to the same location in relation to target areas on or in the body of the wearer a subject's body in repeated use of the garment as long as fastening members remains unopened.

Additionally or alternatively, strap 331 may be fastened to an anterior piece 32 at a plurality of vertical positions, allowing the strap to angle up from the posterior piece (also called posterior portion) 43 to the anterior piece 32. The strap may be fastened such that it would pass highly under the subject's armpit. In such a manner, improved vertical and/or horizontal positioning of the EM transducer units may be provided as the armpit and shoulder are held between strap 331 and the shoulder piece 31. Moreover, pressure may be applied uniformly by this structure (optionally with an added pressure applying element) across the EM transducer unit 339 at locations above the subject's armpits.

Figure 8:
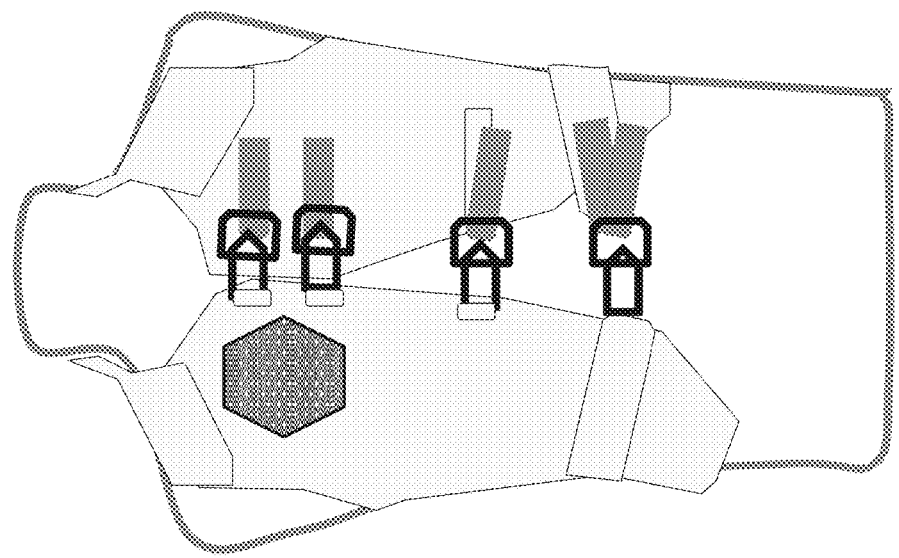
FIG. 8 is a schematic drawing depicting an exemplary garment having a plurality of release buckles, according to some embodiments of the present invention.

Optionally, an additional strap, with higher elasticity and/or lower rigidity than strap 331, is positioned at an even higher vertical location than strap 331, passing closer to the armpit than the strap 331. This may improve the pressure applied on EM transducer unit 339 and optionally the comfort of the wearer. Optionally, the thoracic garment 30 includes a vertical fastening member 35 for defining and optionally locking in position the chest coverage breadth of the anterior piece 31 and/or a relative orientation between the lateral sub pieces to fit the thoracic garment 30 to a wearer's body size and/or shape. The fastening member 35 in anterior piece 32 may bind the lateral sub pieces together at a plurality of alternative horizontal positions. Optionally, in order to facilitate the undressing and/or the wearing of the thoracic garment 30 without refitting of the straps or any other fitting element, the anterior piece 32 is divided to two lateral sub pieces by a simple release fastener (in this example zipper 34) positioned vertically near the horizontal middle of the anterior piece 32. Zipper 34 allows taking the garment off a subject and redressing the subject with the garment without opening and/or adjusting the vertical fastening member 35. Other fasteners may be used instead of the zipper, for example see FIG. 8, which is an exemplary garment having a plurality of release buckles, according to some embodiments of the present invention. In this context, a simple release fastener may be taken to mean a fastener that may be released by the wearer without assistance (at times even if the wearer is physically impaired, for example having diminished and/or limited dexterity) and without need for tools. In some embodiments the fastener is configured for reuse in a plurality of dressing and undressing sessions.

Optionally, as shown at FIG. 9, pulling straps extend from the bottom side of the thoracic garment, for example as shown at 871. These pulling straps may ease the undressing and/or dressing of the relatively tight and non-elastic thoracic garment when grabbed and pulled by the wearer.

Optionally, the thoracic garment 30 includes a belt having one or more belt members 37, 38 to fit the thoracic garment 30 about a wearer's waist for example by adjusting straps length in relation to a belt buckle 371. The belt may further anchor the thoracic garment 30 when worn, for example to reduce or prevent the garment from sliding upwards on a wearer's thorax during a position change, for example when the wearer moves between sitting, standing, lying and/or reclining positions.

Optionally, the thoracic garment 30 includes an undressing detector for detecting an undressing event. The outputs of the undressing detector may be received by a controller which reduces the pressure applied by the pressure applying elements on the body of the wearer. The undressing detector may in some embodiments be a mechanical switch, a pressure switch and/or the like.

Optionally, the thoracic garment 30 includes a horizontal or diagonal zipper 36 traversing one of the lateral pieces from the armpit opening to the center of the anterior piece 32. Such a zipper 36 may be used to divide a lateral sub piece of the anterior piece 32 to top and bottom segments. This may facilitate dressing and/or undressing a wearer wearing the thoracic garment 30 when the arm is connected to a medical instrument, such as infusion.

Optionally, the thoracic garment 30 includes a supporting component 39 for processing EM energy captured by the EM transducer unit(s) in the EM transducer placement pieces 33, 42 and/or for energizing and/or motorizing the pressure applying elements and/or for energizing a controller. Additional technical components may be incorporated in the thoracic garment, optionally interconnected or in communication with each other in a wired and/or wireless manner, providing a coordinated functionality.

Figure 7E:
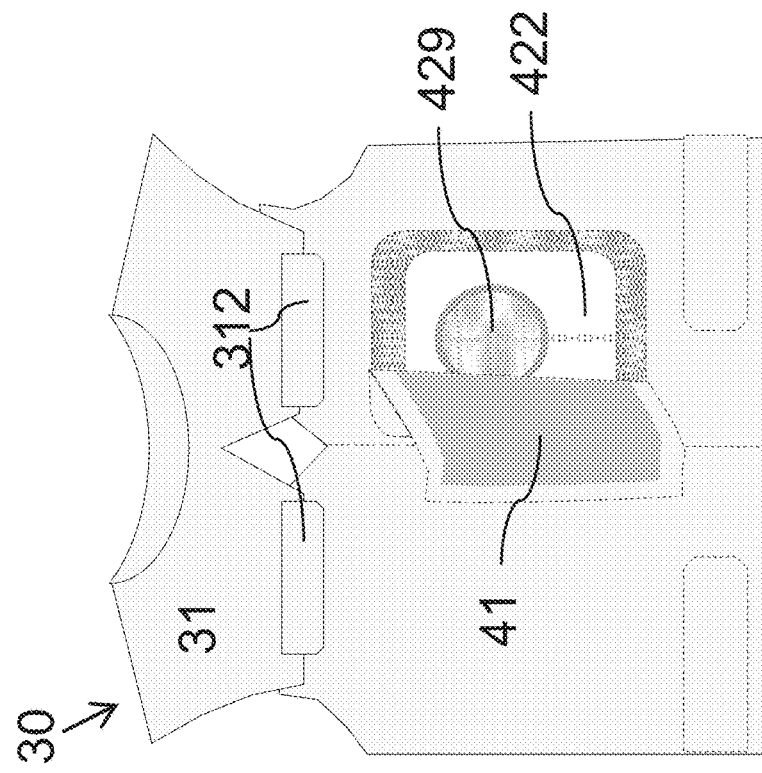

Optionally, one or more of the transducer placement pieces 33, 42 include a flap 41 covering a window area which surrounds the transducer placement pieces 33, 42. For example, FIG. 7E depicts window 422 which is revealed when flap 41 in an open position. EM transducer unit 429 (and/or EM transducer unit 339) may be positioned at a various horizontal and/or vertical locations in the transducer placement pieces 33, 42. This allows positioning of the EM transducer unit 429 (and/or EM transducer unit 339) respective of the subject's body as needed. Optionally, each one of the transducer placement pieces 33, 42 includes a panel that binds the movement of the EM transducer unit so that it remains in contact with the lining of the garment 43.

Additionally or alternatively, one or more EM transducer placement portion(s) 33, 42 or EM transducer unit(s) 339, 429 includes a lateral movement mechanism that allows laterally moving an EM transducer unit within a defined area, for example window 422 or a part thereof. As used herein, lateral movement includes movement in a plane defined to be the space within an EM transducer placement portion, essentially in parallel to the skin surface of the wearer (when worn).

This may be used to facilitate a mechanical positioning of the EM transducer unit within the window area. The mechanical movement may be controlled by an operator and/or a controller device during the fitting of the thoracic garment 30 until reaching a predefined location and locked in position for future wearing sessions.

Additionally or alternatively, a plurality of EM transducer units 339, 429 may be positioned in each of one or more transducer placement portions, for example in the window 422. In such an embodiment, a plurality of EM transducer units may be operated in a selective manner based on the respective location of their antennas in relation to the anterior and/or posterior thoracic skin surface areas. For example, one or more EM transducer units (or an array of EM transducer units) are selected among a plurality of EM transducers according to their position respective the body of a wearer.

In cases where a plurality (optionally an array) of EM transducers and/or a plurality (optionally an array) of antennas within an EM transducer are used, a different pressure may be applied to the different EM transducer units thereby to conform the plurality of EM transducers and/or antennas to the skin surface of a wearer. Optionally, the different pressure may be defined to match a certain organ or portion thereof. Optionally, a single EM transducer unit which employs a plurality of antennas may be used and similarly operated, for example by selecting the most suitable antennas.

The flap 41 covers the EM transducer unit(s) and may be locked in position, for example by sewing and/or by fasteners which require an operator key or are difficult to remove unintentionally. FIG. 7C depicts lining panels 334 and 333, optionally made of a biocompatible fabric for subject safety and/or comfort, to protect the wearer from direct contact with the EM transducer unit and/or the supporting component 39. Such panels may function to prevent unintentional or unauthorized displacement of EM transducer unit structures and/or the supporting component 39 after their positioning.

Optionally, at least a segment of the lining of the thoracic garment 30 is covered with and/or made of and/or comprises one or more EM manipulating material(s). As used herein, an EM manipulating material may mean a material that affects an EM wave and/or field propagation, for example by absorbing and/or dissipating energy, and/or by conducting, being resistive to, isolating, deflecting and/or attenuating EM energy. Examples for EM manipulating materials include EM energy absorptive materials and ferromagnetic materials and/or structures. In some examples the EM manipulating materials are in the form of or embedded in a fabric, for example a fabric comprising resistive fibers or ferromagnetic material comprising fibers. The EM manipulating materials are optionally layered, optionally set in sewed or otherwise connected in patches and/or intertwined and/or embedded in a fabric portion or a layer thereof. EM manipulating material(s) may be taken to mean materials including or consisting of one or more of EM absorptive and/or restrictive and/or conductive materials, and/or resistive sheet and/or fabric, and/or materials having significantly higher permittivity and permeability than air, and/or materials having permittivity and/or permeability with high loss, and/or a construction of materials (or metamaterials) with different impedance for guiding the radiation away from inside body and/or on the periphery of the body.

The inventors conducted an experiment with an exemplary thoracic garment 30 essentially as depicted in FIGS. 7A-7E. In this experiment wearers were first fitted with a thoracic garment 30 and then participated in 15 consecutive sessions where in each session the wearer was dressed (or redressed), with the thoracic garment 30 and was radiated with EM energy by an EM transducer unit placed in one of the EM transducer placement portions. At every redressing, the location of the EM transducer unit on the wearer's body was recorded. The inventors showed in this experiment that the repeated positioning of EM transducer units displayed a high accuracy and/or precision. The repeated positioning was within a maximal distance of about ±25 mm for more than 68% of repositioning attempts were within the aforementioned distance. In fact, it was experimentally shown that the EM transducer was placed within ±2 cm from the predetermined location above the skin of the wearer for at least 50% of repeat wearing sessions without refitting, and even within ±10 mm for at least 68% of the repeat wearing sessions. In fact, for an EM transducer unit placed within the anterior thoracic portion repositioning was obtained within ±5 mm for at least 68% of the repeat wearing sessions and for an EM transducer unit placed within the posterior thoracic portion repositioning was obtained within ±7 mm for at least 68% of the repeat wearing sessions.

As described above, the garment is fitted to the body of a certain wearer in a preliminary fitting session before the first use. For example, a reference is now also made to FIG. 10, which is a flowchart 600 of an exemplary preliminary fitting session, according to some embodiments of the present invention.

First, as shown at 301, one or more reference points are defined and optionally marked on a wearer body, for example on thoracic skin surface areas. These reference points are optionally defined by a fitting protocol defining a distance from a certain organ or bodily reference point, for example a thoracic skin surface area, characterized as a skeletal feature, such as the jugular notch and/or vertebra C7 or any reference point on the body. In some cases the reference point is within a location where the EM transducer unit is to be located, for example any of the thoracic skin surface area described in Table 1.

Optionally, the EM transducer placement portion(s) 33 (as shown in FIG. 7A) or 131 (shown in FIGS. 1A and 1B) or a garment portion holding the EM transducer placement portion(s) 131 having detachable flap(s) and/or transparent segment(s) and/or hole(s) and/or a marked area at the border of a garment portion(s) which allow a fitting operator to view the above mark or the above bodily reference point during at least some steps of the fitting process. Optionally, a bodily reference point can be felt through the garment (e.g. a protruding bone such as vertebra C7 or a protruding sticker attached directly or indirectly to the body).

Now, as shown at 302, the thoracic garment 30 or garment 130 is maneuvered so that an anterior EM transducer placement portion is aligned with one or more anterior reference points on the chest of the wearer. For example, the thoracic garment 30 is maneuvered until a reference point is visible via a see-through segment of the anterior EM transducer placement portion and/or a marked area at the border of a garment portion(s) and/or a reference point is felt via the garments and measured to be at a given location.

Optionally, aligning the thoracic garment 30 may include positioning a shoulder piece, for example shoulder piece 31 in FIG. 7B to be supported around the shoulder and/or around the neck region of the wearer. This may be performed before aligning the thoracic garment 30 commences, irrespective of the reference point(s).

Optionally, as shown at 309, a posterior piece of a thoracic garment 30 which has posterior EM transducer placement portion(s) 131 may be fitted according to marks visible via posterior detachable flap(s) and/or transparent segment(s) and/or hole(s) and/or a marked area at the border of a garment portion(s) and/or a reference point is felt via the garments and measured to be at a given location. Optionally, before or after the posterior piece is located, one or more posterior EM transducer units are placed, essentially as described with respect to the anterior EM transducer. In some embodiments, this step may be performed before or after step 302.

Optionally, as shown at 306, an underarm strap in is stretched in a high underarm position, for example see numeral 83 of FIGS. 6A and 6B. This may be for example a position fitting tightly at the armpit close to the arm, for example no more than 0.5 cm or 1 cm distance between the strap and the arm's site of contact in the armpit. This may be performed in a diagonal manner angling up from the posterior piece of the garment to the anterior piece at a site near the EM transducer placement portion(s), for example as shown in FIG. 6C, optionally to a point on the chest that is higher than the armpit line.

Now, as shown at 304, the anterior piece(s) of the thoracic garment 30, for example numeral 32 of FIG. 7A, are locked in position. For example, one or more shoulder straps 311 in FIG. 7A are adjusted (e.g. by manually pressing hook and loop member(s) of an anterior piece against hook and loop member(s) member(s) of a shoulder piece 31 of the garment). This step may be performed for example together with or after step 302.

As shown at 305, the posterior piece(s) of the thoracic garment 30, for example numeral 43 of FIG. 7B, are vertically locked in position. For example, one or more shoulder straps 311 in FIG. 7A are adjusted (e.g. by manually pressing hook and loop member(s) of a posterior piece against hook and loop member(s) member(s) of a shoulder piece 31 of the garment 30). This may be done for example along with or after step 309 and may be done before, after or along with step 304.

It should be noted that various fasteners may be used in addition or instead of hook and loop member(s), for example zippers, belts and/or belt buckles, hooks and latches, buttons, adhesives, and/or the like. In some embodiments the straps and/or fasteners are selected to be such that the fasteners may be fastened in any of a plurality of positions to allow fitting the garment to a wearer.

As shown at 303 respective EM transducer unit(s) may be positioned in the anterior and/or posterior EM transducer placement portion(s). Alternatively, an EM transducer unit (s) may be positioned in the anterior EM transducer placement portion(s) before 302 and/or 309 are performed, as long as this does not prevent the visibility or feeling of a reference point during performance of 302 and/or 309. Optionally, as shown at 307, the thoracic garment 30 is tightened and locked in position in front of the higher half of the thoracic garment 30 across the chest. For example, a strap attached to anterior and posterior pieces of the thoracic garment 30 may be fastened.

As shown at 308, the thoracic garment may be tightened and locked in position horizontally by one or more straps. Optionally, the thoracic garment 30 is tightened horizontally by one or more straps, thereby allowing a better fit to a vertically changing contour. Optionally, the anterior piece of the thoracic garment 30 comprises two lateral sub pieces set to be attached by a hock and loop fasteners. This may be used to further tighten the thoracic garment 30 once anterior, posterior, and shoulder pieces are essentially secured in position.

Optionally, after the above is performed, straps may be locked in position to maintain the formed size and shape of the thoracic garment 30. This may be performed for example by sewing over fastening members, use of an adhesive, tacks, and/or the like. This may assist in preventing unintentional opening of the thoracic garment 30, for example during the wearing and/or undressing thereof, for example as an outcome of tension exertion.

According to some embodiments of the present invention, the measures of the fitted thoracic garment 30 are taken for allowing the manufacture of a custom-made garment. In such am embodiment, fitted thoracic garment 30 may be used as a measure taking device. Optionally, straps are marked with notches and/or graduations which are indicative of a length and/or elasticity coefficient selected during the fitting session. Additionally or alternatively, the garment is marked, for example outer and/or inner surfaces.

Optionally, the thoracic garment 30 or a garment portion or fabric is made of a substrate having relatively low elasticity coefficient. Examples for substrates having such relatively low elasticity include a substrate that increases in length by 20% or less when a 10 Newton load is applied on one of its edges or a substrate that increases in length by 20% or less when a 15 Newton load is applied on one of its edges (for example when conducting a standard test using a commercially available testing device such as Zwick/Roell BZ2.5/TH1S), and/or a substrate that increases in length by 60% or less when a 3 cm wide strip thereof is held at one edge perpendicular to the axis of gravity a 0.5 Kg or even 1 Kg load is attached to its other edge. This relatively low elasticity coefficient may help in ensuring repeatability of EM transducer unit placement between wearing sessions. Moreover, this relatively low elasticity coefficient reduces the movement of fabric respective the subject's body when the thoracic garment 30 is worn thereby maintaining the EM transducer unit(s) in place when the wearer is moving.

The posterior anterior and/or shoulder pieces of the thoracic garment 30 and/or any other portion of the garment may comprise a plurality of materials, including, in some embodiments, EM manipulating material(s).

Some exemplary thoracic garments may include a number of layers comprising:

1. An inner layer, also referred to as a lining, intended to be in touch with the skin of the wearer and/or an undershirt, for brevity referred to interchangeably. Examples for such materials include unbroken loop (UBL) fabric and/or Breathe-O-Prene™ fabric of AccuMED Innovative Technologies™. It is noted that Breathe-O-Prene™ fabric comprises a biocompatible UBL sublayer and a Lycra sublayer having a polyurethane foam sublayer therebetween. This fabric is has a degree of elasticity and flexibility that is useful for a plurality of embodiments, as well as hook and loop binding capabilities. By covering the Lycra sublayer with an additional UBL sublayer one may have a fabric having hook and loop binding capabilities in both sides.
2. A layer, which may be a layer of patches, which includes a substrate capable of binding other fabrics or materials, such as hook and loop substrate, such as Velcro™. Such a substrate may be attached to the inner layer and/or the outer layer of the thoracic garment and/or located especially in areas intended for binding. These substrates may also be selected to be durable and unstretchable (low elasticity coefficient) so that when bound to its binding member it the garment will retain shape and position despite being under stretching force when worn. Breathe-O-Prene™ and unbroken loop (UBL) fabric are examples for such materials.

According to some embodiments of the present invention, the thoracic garment 30 includes and/or comprises a substrate having EM manipulating material(s) The EM manipulating materials may be attached and/or fused and/or bounded together with a fabric and/or portion of a garment as known in the art. The EM manipulating materials may be located in the proximity of EM transducer units, in selected garment areas, for example between two EM transducer units and/or throughout the thoracic garment 30.

The EM manipulating materials may be placed generally in vicinity of an EM transducer unit and/or along an EM transmission path in the worn garment surface from one transmitting EM transducer unit to another. An exemplary general area is marked in FIG. 7C by dashed line 300. The EM manipulating materials may be placed in the proximity of the skin, optionally separated from the skin by one or more layers of fabric), so as to follow a body contour.

In some embodiments, EM manipulating materials comprise metamaterials. Metamaterials may be structures or a combination of structures of metals or different materials with different permittivity and permeability with or without components with different inductance, reactance, and/or resistive properties integrated into them in a certain structure so as to implement desired impedance. It may comprise a network of resistors with capacitors and coils.

Examples for EM manipulating materials include materials having one or more of the following properties:

Permeability loss tangent of $(\tan \delta = \mu''/\mu') > 0.01$ or $>0.3$ or $>0.6$ for all or some of the frequencies within the range of 100 MHz-5 GHz for example for 1 GHz and/or 2 GHz.

Permittivity loss tangent of $(\tan \delta = \varepsilon''/\varepsilon') > 0.01$ or $>0.3$ or $>0.6$ for all or some of the frequencies within the range of 100 MHz-5 GHz for example for 1 GHz and/or 2 GHz.

Partial conduciveness manifested by a surface resistivity between 20 and 10,000 Ohm per square ($\Omega$/sq) and/or a volumetric resistivity which is $>10^{-3}$ Ohm meter ($\Omega$m). For example, resistive substrates and/or volumetric resistive materials may be constructed from and/or comprised of resistive wiring and/or conductive wires with or without lumped resistors, capacitors, and/or inductance elements.

Optionally, EM manipulating materials are incorporated into the thoracic garment 30 for shielding EM transducer unit(s) from noises, such as foreign EM signals from sources unrelated to the use of the thoracic garment 30 or from transmissions of the system itself that traveled through an undesired path. Optionally, EM manipulating materials are incorporated into the thoracic garment 30 for reducing the sensitivity to noise from proximate EM transducer units, for example from external EM transmission sources, such as cellular phones to improve SNR and therefore quality of reception. The noise may include EM signals produced in connection with the thoracic garment function, for example EM energy transmitted by the EM transducer unit and propagated around the subject's body from a transmitting EM transducer unit to an intercepting EM transducer unit. The noise may be transmitted through air, body tissue(s) for example skin and/or fat, components of the thoracic garment 30, for example conductive fabrics, wiring, and/or other electronic components. EM manipulating materials may be positioned to prevent from at least some EM signals in use by the system to make their way to the external surface of the EM transducer unit. In such a manner, the amount of signals which may add noise to the external environment is reduced. This may also reduce currents the effect of currents traveling on the surface of the lateral and back sides of the EM transducer unit. Such currents may be conducted on the skin, external conductive parts of the EM transducer unit, and/or conducting elements, such as cables. Such currents may, for example, be induced by EM energy related to a transmitting EM transducer unit, or its connected cables, onto the conductive parts, or proximate skin area, of a receiving EM probe, via conduction or induction, resulting in parasitic crosstalk between them.

Optionally, the EM manipulating materials are incorporated into the thoracic garment 30 for reducing energy propagating through alternative pathways, such as pathways that do not traverse or are not affected by target organs and/or tissues having properties of interest. Such pathways may, for example, pass around the body parts, for example via skin, peripheral fat and/or outside the body, for example via air.

Examples for EM manipulating materials include CobalTex™, which is a near field magnetic radio frequency (RF) shielding fabric of Less EMF Inc or Eccosorb™ of Emerson and Cuming Microwave Products. Examples for surface resistive EM manipulating materials includes Statitec™ of 20 ohm/sq or 1000 ohm/sq EMF Inc. and metallic materials, for example a metal foil. Resistive EM manipulating materials may be combined with near field magnetic RF shielding materials. In some embodiments the thoracic garment may comprise materials for absorbing electromagnetic radiation, as disclosed in PCT/IL2011/050003 filed Nov. 3, 2011, which is incorporated herein by reference in entirety.

Additional examples include materials capable of diverting, reflecting disrupting and/or attenuating EM propagation such that EM energy may be released away from the body of the wearer and/or be caused to propagate away from an undesired area within the thoracic garment 30.

Optionally, the EM manipulating materials includes materials which absorb electric fields and/or magnetic fields. Optionally the complex permittivity of such EM manipulating materials at a frequency of about 1 Ghz, $\varepsilon'$ is between 2 and 60 or around 8-30 and $\varepsilon''$ is between 1 and 30 or even 5-10 and regarding the complex permeability of the absorbing material, $\mu'$ is between 1 and 30 or about 20 and $\mu''$ is between 1 and 30 or even 6 to 15. The absorbing material may be Eccosorb® MCS, GDS and BSR, which the specifications thereof are incorporated herein by reference. Optionally, the thickness of the one or more layers and/or patches formed from of EM manipulating materials is between about 0.1 millimeters (mm) and about 20 mm.

Optionally, area between the EM transducer units is covered with the EM manipulating materials. Alternatively, one or more patches of EM manipulating materials separate between the EM transducer units, for example by gaps of between about 1 cm and about 5 cm for EM energy within the frequency range of between 0.5 GHz and 4 GHz and/or with predetermined impedance discontinuities manipulates EM energy propagation. The gaps may allow a part of the EM energy to escape from the garment and not only be absorbed by the EM manipulating materials. Gaps may also reduce the hazard of conducting energy from one EM transducer unit to another. Direct conductance between the EM transducer units via unintended pathways may thus be reduced and/or prevented.

Optionally, area between the EM transducer units is designed to attenuate and/or deflect stray energies, optionally by taking advantage of impedance differences. This may have gaps dimensioned to facilitate escape of energy from the garment and/or to reduce the hazard of conducting energy from one EM transducer unit to another. This area may be in the circumference of EM transducer units and/or along the short path between EM transducer units, for example see dashed line 300 in FIG. 7C.

It is expected that during the life of a patent maturing from this application many relevant methods and systems will be developed and the scope of the term a processor, an antenna, a transducer, and a controller is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A thoracic garment configured for bringing one or more antennas for transmitting and/or intercepting electromagnetic (EM) energy into contact with a thoracic skin surface area of a wearer, comprising:

a thoracic garment having a posterior piece, an anterior piece, and a Y shape strap arrangement comprising two non-elastic straps each having an adjustable length and is not stretched by bodily movements of the wearer, said at least two non-elastic straps are adapted to maintain a location of a placement portion adapted to support at least one EM transducer for transmitting and/or intercepting EM energy in relation to a thoracic skin surface area of the wearer, said two non-elastic straps comprise:

an underarm strap adapted to be placed tightly under an armpit of the wearer and angling up from said posterior piece to a point on said anterior piece that is higher than said armpit, and a shoulder strap adapted to be supported around a shoulder and/or around the neck region of the wearer; and a pressure applying element associated with said EM transducer for applying a pressure on the EM transducer when said thoracic garment is worn by said wearer so that said EM transducer is adapted to apply a respective pressure on a thoracic skin surface area of said wearer.

2. The thoracic garment of claim 1, wherein said pressure applying element comprises a strap configured to attach said thoracic garment to said wearer in one of a plurality of positions each applying a different of a plurality of pressures on said wearer.

3. The thoracic garment of claim 1, further comprising a controller adapted to control a control, said pressure adjusting element is adapted to increase said pressure at least until an anterior surface of said EM transducer is in full surface contact with a skin surface of said wearer, said pressure adjusting element is adapted to maintain said respective pressure during a sensing period.

4. The thoracic garment of claim 3, wherein said controller is set to allow transmitting of EM energy to or by said EM transducer when said pressure is within a predefined range.

5. The thoracic garment of claim 1, wherein said thoracic garment is associated with a controller set to adjust said pressure to maintain said respective pressure above a predetermined threshold during a period of measurements held using said EM transducer.

6. The thoracic garment of claim 1, wherein said respective pressure is between 150 and 500 millibar.

7. The thoracic garment of claim 1, wherein said pressure applying element comprises an extendable member positioned between an anchoring element and said EM transducer, said extendable member having an adjustable length which changes a distance between an anchoring surface and said EM transducer.

8. The thoracic garment of claim 7, wherein said adjustable length is between 2 centimeters (cm) and 5 cm.

9. The thoracic garment of claim 7, wherein said extendable member is an inflatable member and wherein said adjusting includes adjusting a fluid pressure within said inflatable member.

10. The thoracic garment of claim 1, wherein said EM transducer structure comprises an EM transducer tilt matching mechanism.

11. The thoracic garment of claim 1, further comprising a plurality of EM transducers and a plurality of extendable members each positioned between an EM transducer and an anchoring surface such that a different pressure may be applied by one extendible member on a respective EM transducer than is applied on another extendible member on a respective EM transducer.

12. The thoracic garment of claim 11, wherein the plurality of EM transducers are comprised in a single array.

13. The thoracic garment of claim 1, wherein said thoracic garment comprises a non-elastic thoracic portion having width of at least 3 centimeter and extends by no more than 60% of its length when attached to a load weighing 0.5 Kg.

14. A set of thoracic garments, each defined as claimed in claim 1 and each being adjustable to fit different body shape and size.

15. The thoracic garment of claim 1, further comprising an undressing detector for detecting an undressing event, said controller reduces said pressure in response to said undressing event.

16. The thoracic garment of claim 1, further comprising a plurality of fitting elements adapted to allow said wearer to tighten said thoracic garment on the body of said wearer and at least one release fastener adapted to allow said wearer to undress said thoracic garment without refitting said plurality of fitting elements.

17. A thoracic garment for positioning at least one EM transducer on a body of a wearer comprising:
a thoracic garment having a posterior piece, an anterior piece, and a Y shape strap arrangement comprising two non-elastic straps each having an adjustable length and is not stretched by bodily movements of the wearer, said two non-elastic straps are adapted to maintain a location of a placement portion adapted to support at least one EM transducer for transmitting and/or intercepting EM energy in relation to a thoracic skin surface area of the wearer, said two non-elastic straps comprise:
an underarm strap adapted to be placed tightly under an armpit of the wearer and angling up from said posterior piece to a point on said anterior piece that is higher than said armpit, and
a shoulder strap adapted to be supported around a shoulder and/or around the neck region of the wearer,
wherein said thoracic garment is sized and shaped to position said at least one EM transducer at a predetermined location above a skin surface of said wearer; and
a controller adapted to increase pressure of said at least one EM transducer on said skin surface after the thoracic garment is worn and reduces said pressure when said wearer undresses said thoracic garment;
wherein when said pressure is reduced a physically impaired wearer can self-dress the thoracic garment.

18. The thoracic garment of claim 17, further comprising an EM transducer secured in said EM transducer placement portion.

19. The thoracic garment of claim 18, wherein said EM placement portion is associated with an EM transducer moving mechanism for moving an EM transducer or a portion thereof within the EM transducer placement portion.

20. The thoracic garment of claim 18, wherein said EM transducer is one of a plurality of EM transducers located in a plurality of EM transducer placement portions and the thoracic garment comprises a controller for selecting one or more of said plurality of EM transducers according to the position of the EM transducers respective a body of a wearer.

21. The thoracic garment of claim 17, wherein the thoracic garment portion is adjustable to fit a body shape and size of a wearer.

22. The thoracic garment of claim 17, wherein when the thoracic garment portion is worn by a wearer to whom it was fitted, and at least one EM transducer is placed in said EM transducer placement portion, the at least one EM transducer is placed within ±2 cm from the predetermined location above the skin of the wearer for at least 50% of repeat wearing sessions without refitting.

23. A thoracic garment for bringing an EM transducer into contact with a thoracic skin surface area of a wearer, comprising:
a thoracic garment having a posterior piece, an anterior piece, and a Y shape strap arrangement comprising two non-elastic straps each having an adjustable length and is not stretched by bodily movements of the wearer, said two non-elastic straps are adapted to maintain a location of a placement portion adapted to support at least one EM transducer for transmitting and/or intercepting EM energy in relation to a thoracic skin surface area of the wearer, said two non-elastic straps comprise:
an underarm strap adapted to be placed tightly under an armpit of the wearer and angling up from said posterior piece to a point on said anterior piece that is higher than said armpit, and
a shoulder strap adapted to be supported around a shoulder and/or around the neck region of the wearer; and
a pressure applying element associated with said EM transducer for applying a pressure on the EM transducer when said thoracic garment is worn by said wearer so that said EM transducer is adapted to apply a respective pressure on a thoracic skin surface area of said wearer;
wherein said EM transducer placement portion is set to be placed above the skin surface of a posterior thoracic skin surface area such that at least 30% of an effective EM capture and/or transmission area of an EM transducer positioned in the EM transducer placement portion will be located between 2 cm and 9 cm to a side of a central axis along the spine of said wearer, and between about 8 cm and about 30 cm below the upper end of the vertebra prominens of said wearer;
wherein when worn said wearer can recline and sit up freely while an effective EM capture and/or transmission area of said EM transducer is not displaced by more than 2 centimeters (cm).

* * * * *